United States Patent [19]
Ishizuka et al.

[11] Patent Number: 5,527,820
[45] Date of Patent: Jun. 18, 1996

[54] ANTIBIOTICS HAVING IMMUNOSUPPRESSIVE ACTIVITY, DELAMINOMYCINS AND PROCESSES FOR THE PRODUCTION OF THE SAME

[75] Inventors: Masaaki Ishizuka, Mishima; Mitsuhiro Ueno, Numazu; Hironobu Iinuma, Wako; Hiroshi Naganawa, Tokyo; Masa Hamada, Naito-machi; Kenji Maeda; Tomio Takeuchi, both of Tokyo, all of Japan

[73] Assignee: Zaidan Hojin Biseibutsu Kagaku Kenkyu Kai, Tokyo, Japan

[21] Appl. No.: 356,267

[22] PCT Filed: Jun. 22, 1993

[86] PCT No.: PCT/JP93/00845

§ 371 Date: Jan. 20, 1995

§ 102(e) Date: Jan. 20, 1995

[87] PCT Pub. No.: WO94/00430

PCT Pub. Date: Jun. 1, 1994

[30] Foreign Application Priority Data

Jun. 23, 1992 [JP] Japan ................................. 4-187403
Apr. 8, 1993 [JP] Japan ................................. 5-104921

[51] Int. Cl.$^6$ ........................ A61K 31/40; C07D 207/36
[52] U.S. Cl. ........................ 514/423; 548/539; 435/121
[58] Field of Search ........................ 548/539; 514/423; 435/121

[56] References Cited

PUBLICATIONS

Ueno et al., J. Antibiotics, (1993), 46(5), 719–27.

*Primary Examiner*—Johann Richter
*Assistant Examiner*—Laura R. Cross
*Attorney, Agent, or Firm*—Larson and Taylor

[57] ABSTRACT

As new antibiotics are obtained delaminomycins A, B and C having a formula (I) or (I') shown below, or salts thereof. Delaminomycins preferentially inhibit T cells and are useful as immunosuppressants, antineoplastic agents and antibacterial agents.

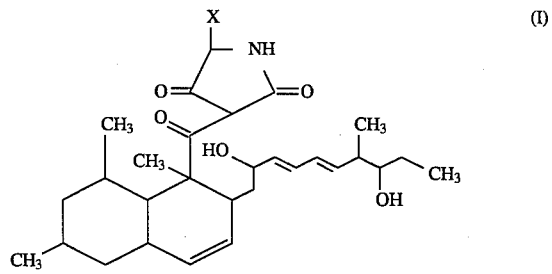

wherein X is a hydroxyl group for delaminomycin A, a methoxy group for delaminomycin B and a hydrogen atom for delaminomycin C.

5 Claims, 7 Drawing Sheets

ANTIBIOTICS HAVING IMMUNOSUPPRESSIVE ACTIVITY, DELAMINOMYCINS AND PROCESSES FOR THE PRODUCTION OF THE SAME

This application is a 371 of PCT/JP93/00845 filed Jun. 22, 1993.

TECHNICAL FIELD

This invention relates to new antibiotics, delaminomycins, which have an immunosuppressive activity and also have an antibacterial activity and an antineoplastic activity. This invention also relates to processes for the production of these antibiotics.

More particularly, this invention relates to delaminomycin A, delaminomycin B, delaminomycin C, delaminomycin A2, delaminomycin B2 and delaminomycin C2 which are the new antibiotics having an immunosuppressive activity, an antibacterial activity to Gram-positive bacteria and an antineoplastic activity, as well as pharmaceutically acceptable salts of the delaminomycins. This inventions also relates to processes for the production of these new antibiotics. Further, this invention relates to a pharmaceutical composition, especially an immunosuppressant composition which comprises the new antibiotic(s) as an active ingredient. Furthermore, this invention relates to sulfuric acid esters of delaminomycins A2, B2 and C2 or salts thereof.

The above-mentioned delaminomycin A, delaminomycin B, delaminomycin C, delaminomycin A2, delaminomycin B2 and delaminomycin C2 are the antibiotics which were named the antibiotics MJ202-72F3-A, MJ202-72F3-B, MJ202-72F3-C, MJ202-72F3-A', MJ202-72F3-B' and MJ202-72F3-C', respectively, at the time which we, the present inventors, initially succeeded in obtaining these new antibiotics. These new antibiotics are described under the laboratory designations, MJ202-72F3, in the specification of Japanese patent application No. 187403/92 (filed 23 Jun. 1992), though the new names of delaminomycins are recently employed by us in stead of the names of MJ202-72F3.

BACKGROUND ART

Hitherto, cyclosporin A, FK506 and spergualins etc., are known as the immunosuppressive substances which are produced by microorganisms. However, these known substances are not fully satisfactory as immunosuppressant.

For many years, there have been demands to provide a new immunosuppressive substance which is useful for transplantation of organs and for therapeutic treatments of immuno-defficiency diseases and local inflammations and is superior to the known immunosuppressants, and to provide a substance which has an excellent antineoplastic activity.

DISCLOSURE OF THE INVENTION

In an attempt to find useful substances having an immunosuppressive activity in the microbial products, we, the present inventors, have isolated a number of microorganisms out of naturally occurring soils and conducted extensive research on the products of these microorganisms. As a result, we have found that three antibiotics, which have an excellent immunosuppressive activity and initially are named as the MJ202-72F3-A, -B and -C substances, are produced and accumulated in a culture broth of a microorganism which we newly have isolated from a soil sample and which belongs to the genus *Streptomyces*. We have isolated these substances and investigated the biological and physico-chemical properties of these substances. And we have found that these substances have an immunosuppressive activity, an antibacterial activity against Gram-positive bacteria and an anti-neoplastic activity, and that these substances are new compounds as determined through elucidation of their chemical structure formulae and include tautomers.

As mentioned hereinbefore, the substances MJ202-72F3-A, -B and -C substances have recently been re-named as delaminomycin A, delaminomycin B and delaminomycin C, respectively.

Moreover, we have employed each of the above-mentioned delaminomycins A, B and C as a starting material and succeeded in producing delaminomycin A2 from delaminomycin A, delaminomycin B2 from delaminomycin B and delaminomycin C2 from delaminomycin C, respectively, by subjecting the starting materials to a chemical process comprising a ring-closure reaction with accompanying dehydration. We have further investigated biological and physico-chemical properties of delaminomycins A2, B2 and C2 and found that these substances have an immunosuppressive activity, an antibacterial activity against Gram-positive bacteria and an antineoplastic activity and they are also new compounds as determined through elucidation of their chemical structure formulae.

Thus, this invention provides delaminomycins A, B and C as well as delaminomycins A2, B2 and C2 of which each substance is a new antibiotic having an immunosuppressive activity, an antibacterial activity and an antineoplastic activity, and also this invention provides processes for the production of these substances.

More particularly, in a first aspect of this invention, there are provided new antibiotics having an immunosuppressive activity, delaminomycin A, delaminomycin B and delaminomycin C represented by the following general formula (I)

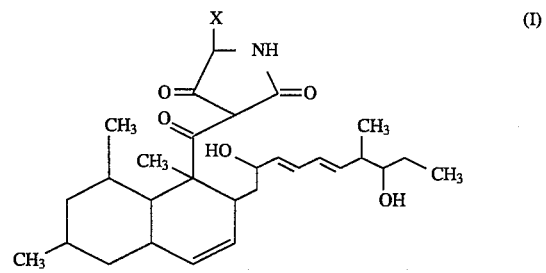

or by the following general formula (I')

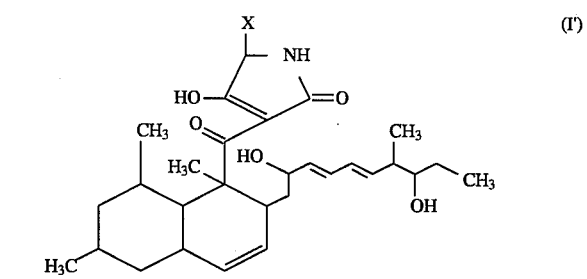

wherein X denotes a hydroxyl group, methoxy group or hydrogen atom, but X is a hydroxyl group for delaminomycin A, a methoxy group for delaminomycin B and a hydrogen atom for delaminomycin C, or salts thereof.

The compound as represented by the general formula (I) and the compound as represented by the general formula (I') exist mutually in a relationship of tautomerism. Further, the salts of delaminomycins A, B or C having the general formula (I) or general formula (I') include such salts which may be a salt with a pharmaceutically acceptable metal, for example, a salt with an alkali metal such as sodium and potassium; a salt with an alkaline earth metal such as calcium; or an ammonium salt.

In a second aspect of this invention, there are further provided new antibiotics having an immunosuppressive activity, delaminomycin A2, delaminomycin B2 and delaminomycin C2 represented by the following general formula (II)

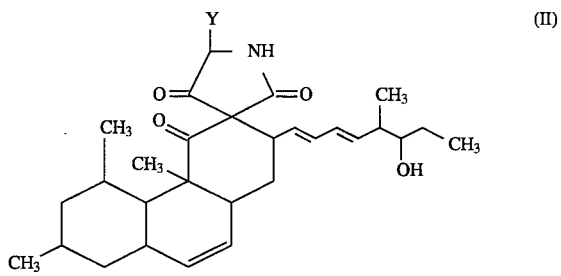

wherein Y denotes a hydroxyl group, methoxy group or hydrogen atom, but Y is a hydroxyl group for delaminomycin A2, a methoxy group for delaminomycin B2 and a hydrogen atom for delaminomycin C2.

[1] Physico-chemical properties of delaminomycins A, B and C (a) Delaminomycin A according to the first aspect of this invention, which is a compound of the general formula (I) or (I') where X is a hydroxyl group, has the following physico-chemical properties:

(1) Color and appearance of the substance: colorless to white, solid.

(2) Empirical formula: $C_{29}H_{43}O_6N$ (3) Elementary analysis: for $C_{29}H_{43}O_6N \cdot H_2O$

|  | C | H | O | N |
|---|---|---|---|---|
| Found: | 67.37% | 8.79% | 21.22% | 2.61% |
| Calculated: | 67.03% | 8.73% | 21.55% | 2.70% |

(4) Molecular weight: 501

(5) FAB (Fast Atom Bombardment) mass spectrum: m/z 500 [M–H]⁻ is observed.

(6) Ultraviolet absorption spectrum: the following absorption peaks are shown when measured in a methanolic solution. $\lambda_{max}^{MeOH}$ nm ($E_{1\ cm}^{1\%}$) : 232(728), 288(208)

(7) Infrared absorption spectrum (KBr method): as shown in FIG. 1 of the accompanying drawings. $v_{max}^{KBr}$ : 3400, 2950, 2900, 1660, 1590, 1430, 1100, 950 cm⁻¹

(8) ¹H-NMR spectrum (400 MHz): δ 6.13(1H, dd), 5.80(1H, m), 5.79(1H, m) 5.57(1H, dd), 5.48(1H, dd), 5.39(1H, m), 4.82(1H, s), 4.03(1H, m), 3.27(1H, br), 3.22(1H, m), 2.17(1H, m), 1.90(1H, m), 1.81(2H, m), 1.78(1H, m), 1.71(1H, m), 1.63(1H, m), 1.50(3H, s), 1.48(1H, m), 1.30(1H, m), 1.28(1H, m), 1.11(1H, m), 1.06(1H, m), 0.99(3H, d), 0.92(3H, d), 0.91(3H, dd), 0.91(1H, m), 0.84 (3H, d)

The ¹H-NMR spectrum is measured in deutero-methanol using methanol (3.30 ppm) as a standard substance.

(9) ¹³C-NMR spectrum (100 MHz): δ 204.8s, 192.9s, 181.5s, 138.1d, 137.1d, 131.6d, 131.0d, 130.8d, 129.1d, 101.3s, 79.7d, 78.1d, 71.6d, 51.5s, 48.3t, 45.5d, 44.3d, 44.3t, 43.6t, 43.5d, 40.5d, 37.2d, 35.7d, 28.3t, 24.3q, 22.9q, 16.5q, 15.4q, 11.0q The ¹³C-NMR spectrum is measured in deutero-methanol using methanol (49.00 ppm) as a standard substance.

(10) Solubility: soluble in methanol but slightly soluble or insoluble in water, acetone, ethyl ether and n-hexane.

(11) Thin layer chromatography (on Silica Gel 60F₂₅₄ Art. 5554, manufactured by Merck Co.): Rf value is shown in a table below.

| Developing solvent system | Rf value |
|---|---|
| 2-Propanol-aqueous ammonia-water (9:1:2) | 0.49 |

(12) Color reaction: positive to vanillin-sulfuric acid and anisaldehyde-sulfuric acid.

(b) Delaminomycin B according to the first aspect of this invention, which is a compound of the general formula (I) or (I') where X is a methoxy group, has the following physico-chemical properties:

(1) Color and appearance of the substance: colorless to white, solid.

(2) Empirical formula: $C_{30}H_{45}O_6N$ (3) Molecular weight: 515

(4) FAB (Fast Atom Bombardment) mass spectrum: m/z 514 [M–H]⁻ is observed.

(5) Ultraviolet absorption spectrum: the following absorption peaks are shown when measured in a methanolic solution. $\lambda_{max}^{MeOH}$ nm ($E_{1\ cm}^{1\%}$) : 232(563), 288(138)

(6) Infrared absorption spectrum (KBr method): as shown in FIG. 2 of the accompanying drawings. $v_{max}^{KBr}$ : 3400, 2950, 2900, 1670, 1600, 1430, 1400, 1100 cm⁻¹

(7) ¹H-NMR spectrum(400 MHz): δ 6.10(1H, dd), 5.99(1H, dd), 5.77(1H, m), 5.57(1H, dd), 5.50(1H, dd), 5.40(1H, m), 4.77(1H, s), 4.02(1H, m), 3.28(3H, s), 3.22(1H, m), 2.99(1H, br), 2.17(1H, m), 1.80(1H, m), 1.79(1H, m), 1.77(1H, m), 1.64(1H, m), 1.62(1H, m), 1.53(1H, m), 1.47(1H, m), 1.41(3H, s), 1.34(1H, m), 1.29(1H, m), 1.21(1H, m), 1.02(1H, m), 1.00(3H, d), 0.92(3H, dd), 0.91(3H, d), 0.88(1H, m), 0.72(3H, d)

The ¹H-NMR spectrum is measured in deutero-methanol using methanol(3.30 ppm) as a standard substance.

(8) ¹³C-NMR spectrum (100 MHz): δ 204.2s, 189.2s, 179.6s, 137.8d, 136.7d, 131.0d, 131.0d, 130.6d, 128.6d, 104.4s, 86.1d, 77.9d, 71.0d, 52.6q, 51.6s, 47.8t, 46.4d, 44.3d, 44.2t, 43.8t, 41.9d, 38.6d, 38.6d, 34.8d, 28.4t, 23.7q, 16.4q, 16.4q, 10.7q The ¹³C-NMR spectrum is measured in deutero-methanol using methanol (49.00 ppm) as a standard substance.

(9) Solubility: soluble in methanol but slightly soluble or insoluble in water, acetone, ethyl ether and n-hexane.

(10) Thin layer chromatography (on Silica Gel 60F₂₅₄ Art. 5554, manufactured by Merck Co.): Rf value is as shown in a table below.

| Developing solvent system | Rf value |
|---|---|
| 2-Propanol-aqueous ammonia-water (9:1:2) | 0.74 |

(11) Color reaction: positive to vanillin-sulfuric acid and anisaldehyde-sulfuric acid (c) Delaminomycin C according to the first aspect of this invention, which is a compound of the general formula (I) or (I') where X is hydrogen, has the following physico-chemical properties:

(1) Color and appearance of the substance: colorless to white, solid.

(2) Empirical formula: $C_{29}H_{43}O_5N$ (3) Molecular weight: 485

(4) FAB (Fast Atom Bombardment) mass spectrum: m/z 484 [M–H]⁻ is observed.

(5) Ultraviolet absorption spectrum: the following absorption peaks are shown when measured in a methanolic solution. $\lambda_{max}^{MeOH}$ nm ($E_{1\ cm}^{1\%}$) : 232(530), 286(144)

(6) Infrared absorption spectrum (KBr method): as shown in FIG. 3 of the accompanying drawings. $v_{max}^{KBr}$ : 3400, 2950, 2900, 1650, 1560, 1430, 1400, 900 cm$^{-1}$ (7) $^1$H-NMR spectrum ( 400 MHz ): δ 6.02(1H, dd), 6.01(1H, dd), 5.80(1H, m), 5.58(1H, dd), 5.48(1H, dd), 5.47(1H, m), 4.07(1H, m), 3.72(2H, br, s), 3.24(1H, m), 2.82(1H, br), 2.18(1H, m), 1.86(1H, m), 1.82(1H, m), 1.69(1H, m), 1.69(1H, m), 1.66(1H, m), 1.53(1H, m), 1.53(3H, s), 1.47(1H, m), 1.41(1H, m), 1.30(1H, m), 1.26(1H, m), 1.12(1H, m), 1.01(3H, d), 0.94(3H, d), 0.94(3H, dd), 0.91(1H, m), 0.78(3H, d)

The $^1$H-NMR spectrum is measured in deutero-methanol using methanol(3.30 ppm) as a standard substance.

(8) $^{13}$C-NMR spectrum (100 MHz): δ 203.3s, 192.6s, 179.8s, 138.2d, 136.4d, 131.5d, 130.9d, 130.9d, 128.0d, 103.0s, 77.9d, 70.5d, 51.1t, 50.5s, 47.6t, 45.5d, 44.3d, 44.3d, 44.0t, 43.7t, 42.3d, 38.9d, 34.9d, 28.4t, 23.5q, 22.8q, 16.3q, 16.3q, 10.7q The $^{13}$C-NMR spectrum is measured in deutero-methanol using methanol(49.00 ppm) as a standard substance.

(9) Solubility: soluble in methanol but slightly soluble or insoluble in water, acetone, ethyl ether and n-hexane.

(10) Thin layer chromatography (on Silica Gel 60F$_{254}$ Art. 5554, manufactured by Merck Co.): Rf value is as shown in a table below.

| Developing solvent system | Rf value |
| --- | --- |
| 2-Propanol-aqueous ammonia-water (9:1:2) | 0.77 |

(11) Color reaction: positive to vanillin-sulfuric acid and anisaldehyde-sulfuric acid.

(d) Delaminomycin A2 according to the second aspect of this invention, which is a compound of the general formula (II) where Y is a hydroxyl group, has the following pysico-chemical properties:

(1) Color and appearance of the substance: colorless to white, solid.

(2) Empirical formula: $C_{29}H_{41}O_5N$ (3) Elementary analysis: for $C_{29}H_{41}O_5N$

|  | C | H | O | N |
| --- | --- | --- | --- | --- |
| Found: | 71.22% | 8.46% | 16.91% | 3.28% |
| Calculated: | 72.02% | 8.54% | 16.54% | 2.90% |

(4) Molecular weight: 483

(5) FAB (Fast Atom Bombardment) mass spectrum: m/z 482 [M–H]$^-$ and 636 [M+NBA]$^+$ are observed.

(6) Ultraviolet absorption spectrum: the following absorption peak is shown when measured in a methanolic solution. $\lambda_{max}^{MeOH}$ nm ($E_{1\ cm}^{1\%}$) : 231(614)

(7) Infrared absorption spectrum (KBr method): as shown in FIG. 4 of the accompanying drawings. $v_{max}^{KBr}$ : 3350, 2950, 2900, 1790, 1700, 1600, 1450, 1250, 1080, 990 cm$^{-1}$ (8) $^1$H-NMR spectrum (400 MHz): δ 6.04(1H, dd), 5.96(1H, dd), 5.61(1H, dd), 5.58(1H, m), 5.46(1H, dd), 5.42(1H, dd), 5.39(1H, s), 3.44(1H, m), 2.98(1H, ddd), 2.53(1H, ddd), 2.38(1H, dd), 2.31(1H, m), 2.01(1H, m), 1.82(1H, m), 1.74(2H, m), 1.57(2H, m), 1.50(2H, m), 1.36(1H, m), 1.11(3H, s), 0.98(1H, m), 0.97(3H, d), 0.94(3H, dd), 0.94(1H, m), 0.88(3H, d), 0.70(3H, d)

The $^1$H-NMR spectrum is measured in deutero-chloroform using tetramethylsilane(TMS) (0 ppm) as a standard substance.

(9) $^{13}$C-NMR spectrum (100 MHz): δ 212.2s, 205.5s, 168.6s, 137.4d, 133.8d, 130.7d, 130.0d, 128.9d, 126.8d, 79.5d, 76.7d, 72.5s, 54.4s, 47.3t, 46.1d, 44.1d, 43.7d, 42.3t, 42.0d, 40.4d, 35.6d, 33.1d, 32.0t, 26.4t, 22.1q, 19.0q, 17.1q, 14.2q, 10.6q The $^{13}$C-NMR spectrum is measured in deutero-chloroform using deutero-chloroform (77.00 ppm) as a standard substance.

(10) Solubility: soluble in methanol, ethyl acetate, chloroform and ethyl ether but slightly soluble or insoluble in n-hexane and water.

(11) Thin layer chromatography (on Silica Gel 60F$_{254}$ Art. 5554, manufactured by Merck Co.): Rf values are as shown in a table below.

| Developing solvent system | Rf value |
| --- | --- |
| 2-Propanol-aqueous ammonia-water (40:10:1) | 0.67 |
| n-Hexane-chloroform-acetonitrile (3:2:1) | 0.16 |

(12) Color reaction: positive to vanillin-sulfuric acid and anisaldehyde-sulfuric acid.

(e) Delaminomycin B$_2$ according to the second aspect of this invention, which is a compound of the general formula (II) where Y is a methoxy group, has the following physico-chemical properties:

(1) Color and appearance of the substance: colorless to white, solid.

(2) Empirical formula: $C_{30}H_{43}O_5N$ (3) Molecular weight: 497

(4) FAB (Fast Atom Bombardment) mass spectrum: m/z 498 [M+H]$^+$ and 496 [M–H]$^-$ are observed.

(5) Ultraviolet absorption spectrum: the following absorption peak is shown when measured in a methanolic solution. $\lambda_{max}^{MeOH}$ nm ($E_{1\ cm}^{1\%}$) : 232(588)

(6) Infrared absorption spectrum (KBr method): as shown in FIG. 5 of the accompanying drawings. $v_{max}^{KBr}$ : 3400, 2950, 2900, 1785, 1700, 1455, 1380, 1260, 1080, 970 cm$^{-1}$ (7) $^1$H-NMR spectrum(400 MHz): δ 6.03(1H, m), 5.92(1H, m), 5.60(1H, m), 5.58(1H, m), 5.45(1H, m), 5.41(1H, m), 5.20(1H, s), 3.45(3H, s), 3.36(1H, m), 2.99(1H, m), 2.55(1H, m), 2.34(1H, dd), 2.26(1H, m), 2.02(1H, m), 1.82(1H, m), 1.74(1H, m), 1.71(1H, m), 1.57(1H, m), 1.55(1H, m), 1.50(1H, m), 1.49(1H, m), 1.34(1H, m), 1.10(3H, s), 1.00(1H, m), 0.99(3H, d), 0.95(1H, m), 0.94(3H, dd), 0.87(3H, d), 0.69(3H, d)

The $^1$H-NMR spectrum is measured in deutero-chloroform using TMS (0 ppm) as a standard substance.

(8) $^{13}$C-NMR spectrum (100 MHz): δ 212.2s, 203.9s, 168.7s, 137.5d, 134.2d, 130.6d, 129.8d, 128.7d, 127.0d, 85.3d, 76.5d, 72.5s, 54.9q, 54.4s, 47.3t, 46.1d, 44.1d, 43.9d, 42.4t, 42.4d, 40.5d, 35.5d, 33.1d, 32.3t, 27.0t, 22.1q, 19.0q, 17.2q, 14.8q, 10.3q The $^{13}$C-NMR spectrum is measured in deutero-chloroform using deutero-chloroform (77.00 ppm) as a standard substance.

(9) Solubility: soluble in methanol, ethyl acetate, chloroform and ethyl ether but slightly soluble or insoluble in n-hexane and water.

(10) Thin layer chromatography (on Silica Gel 60F$_{254}$ Art. 5554, manufactured by Merck Co.): Rf value is as shown in a table below.

| Developing solvent system | Rf value |
| --- | --- |
| Chloroform-methanol-aqueous ammonia (40:10:1) | 0.78 |

(11) Color reaction: positive to vanillin-sulfuric acid and anisaldehyde-sulfuric acid.

(f) Delaminomycin C2 according to the second aspect of this invention, which is a compound of the general formula (II) where Y is hydrogen, has the following physico-chemical properties:

(1) Color and appearance of the substance: colorless to white, solid.

(2) Empirical formula: $C_{29}H_{41}O_4N$ (3) Molecular weight: 467

(4) FAB (Fast Atom Bombardment) mass spectrum: m/z 468 $[M+H]^+$ and 466 $[M-H]^-$ are observed.

(5) Ultraviolet absorption spectrum: the following absorption peak is shown when measured in a methanolic solution. $\lambda_{max}^{MeOH}$ nm ($E_1{}_{cm}^{1\%}$) : 230(708)

(6) Infrared absorption spectrum (KBr method): as shown in FIG. 6 of the accompanying drawings. $v_{max}^{KBr}$ : 3380, 2950, 2900, 1780, 1695, 1455, 1380, 1265, 995 $cm^{-1}$ (7) $^1$H-NMR spectrum(400 MHz): δ 6.02(1H, dd), 5.95(1H, m), 5.60(1H, dd), 5.58(1H, m), 5.44(1H, dd), 5.41(1H, m), 3.98(1H, d), 3.64(1H, dd), 3.38(1H, m), 2.98(1H, ddd), 2.56(1H, dd), 2.48(1H, dd), 2.27(1H, m), 2.02(1H, m), 1.82(1H, m), 1.76(1H, m), 1.69(1H, m), 1.60(1H, m), 1.56(1H, m), 1.54(1H, m), 1.51(1H, m), 1.34(1H, m), 1.12(3H, s), 1.00(1H, m), 1.00(3H, d), 0.95(3H, dd), 0.91(1H, m), 0.88(3H, d), 0.70(3H, d)

The $^1$H-NMR spectrum is measured in deutero-chloroform using TMS (0 ppm) as a standard substance.

(8) $^{13}$C-NMR spectrum (100 MHz): δ 211.7s, 205.4s, 170.2s, 137.5d, 133.8d, 130.7d, 129.9d, 128.8d, 127.0d, 76.5d, 71.4s, 54.3s, 51.7t, 47.4t, 46.2d, 45.0d, 43.5d, 42.4t, 42.3d, 40.5d, 35.6d, 33.2d, 32.0t, 27.0t, 22.2q, 19.0q, 17.3q, 14.5q, 10.5q The $^{13}$C-NMR spectrum is measured in deutero-chloroform using deutero-chloroform (77.00 ppm) as a standard substance.

(9) Solubility: Soluble in methanol, ethyl acetate and chloroform but slightly soluble or insoluble in n-hexane and water.

(10) Thin layer chromatography (on Silica Gel 60F$_{254}$ Art. 5554, manufactured by Merck Co.): Rf value is as shown in a table below.

| Developing solvent system | Rf value |
| --- | --- |
| Chloroform-methanol-aqueous ammonia (40:10:1) | 0.80 |

(11) Color reaction: positive to vanillin-sulfuric acid and anisaldehyde-sulfuric acid.

[2] Biological properties of delaminomycins A, B, C, A2, B2 and C2

Each of delaminomycins A, B and C as well as delaminomycins A2, B2 and C2 according to this invention is found to have an antibacterial activity to Gram-positive bacteria.

Spleen cells comprise T cells (also called T-lymphocyte) which participate in the cell-mediated immunity, and B cells (also called B-lymphocyte) which participate in the immunity based on the production of antibody. It is known that when the T cells contained in the spleen cells are treated with Concanavalin A, a mitogen, which acts preferentially on the T cells, the T cells can be activated to involve the reactions of blast formation or blastogenesis and proliferation of the cells. In contrast, it is known that even when the B cells are treated with Concanavalin A, the B cells can neither be activated nor proliferate. The extent of the reaction that the spleen cells containing such T cells as activated by the Concanavalin A treatment can proliferate may be estimated by determining the quantity of $^3$H-thymidine being incorporated into the T cells.

Whether or not a compound has an activity inhibitory to the cell-mediated immunity by the T cells, it can be estimated by determining such degree at which said compound can inhibit the reaction of proliferation of the spleen cells occurring when the spleen cells as treated with Concanavalin A are incubated in the presence of said compound [see referential literature 1: Larson, E, L. et al. "Mechanism of T cell activation. I. A screening of "step one" ligands", the "Eur J Immunol." Vol 10, pp 93–99 (1980), and referential literature 2: Ueno, M. et al, "Dethymicin, a novel immunosuppressant isolated from an Amycolatopsis. Fermentation, isolation, physico-chemical properties and biological activities.", the "J Antibiot." Vol. 45, pp. 1819–1826 (1992)].

Through "in vitro" tests, it has now been found that delaminomycins A, B, C, A2, B2 or C2 according to this invention exhibit an activity inhibitory to the reaction of proliferation of mouse spleen cells which have been activated by the treatment with Concanavalin A.

Furthermore, it is known that when such spleen cells (lymphocytes) as isolated from inbled mouse strain are mixed with such spleen cells (lymphocytes) which have been isolated from another inbled mouse strain and which preliminarily have been treated with mitomycin C and thus enabled to act as the stimulator cell, and when the cell mixture so obtained is subsequently incubated, the T cells contained in the former spleen cells (the responder cell) as isolated from the first mouse strain can be activated to involve the blast formation or blastogenesis and involve the reaction that said T cells proliferate.

The reaction mentioned just above is called the mixed lymphocyte culture reaction. For the mixed lymphocyte culture reaction, it is known that when the mixed lymphocytes are incubated in the presence of such a compound which has an activity to inhibit preferentially the T cells and which has been added into the culture medium wherein the incubation of the mixed lymphocytes is effected, said compound can inhibit the reaction of proliferation of the histocompatibility antigen-dependent T cell taking place in the mixed lymphocyte culture reaction [see referential literature 1: Ishizuka, M. et al. "Induction of antitumor resistance to mouse leukemia L 1210 by spergualins,", the "J. Antibiot." Vol. 39. pp. 1736–1743 (1986) and referential literature 2: Ueno, M. et al. "Dethymicin, a novel immunosuppressant isolated from an Amycolatopsis. Fermentation, isolation, physico-chemical properties and biological activities", the "J. Antibiot." Vol. 45, pp. 1819–1826 (1992)].

It has now been found that delaminomycins A, B, C, A2, B2 and C2 according to this invention have an activity to inhibit the reaction of proliferation of the T cells which act as the responder cell in the "in vitro" test of the mixed lymphocyte culture reaction.

Moreover, it is also known that, by utilizing such phenomenon that a delayed-type hypersensitivity (DTH) will take place by subjecting a mouse as immunized by first injection of sheep red blood cells as antigen, to a second injection of sheep red blood cells, a test can be made to estimate if a compound has an activity to inhibit the cell-mediated immunity [see referential literature 1: the "J. Antibiot." Vol. 33, pp. 642–652 (1990) and referential literature 2: the "J. Antibiot." Vol. 45, pp. 1819–1826 (1992)].

Through the "in vivo" tests of estimating the delayed-type hypersensitivity in mice having received injections of sheep red blood cells as antigen, the delaminomycins according to this invention are found to have an activity inhibitory to the delayed-type hypersensitivity. While, the delaminomycins do not exhibit at all any inhibitory activity in the tests for the production of antibody in which the B cells participate. Accordingly, it is shown that the delaminomycins having the general formula (I) or (I') and the delaminomycins having the general formula (II) according to this invention have an immunosuppressive activity and also have an antibacterial activity.

From the above results, we have found that the delaminomycins according to this invention have an activity to inhibit preferentially the T cells. Delaminomycins have their uses as an immunosuppressant required for the transplantation of organs, and also as a drug useful for a therapeutic treatment of auto-immune diseases which are a state of hyper-sensitive immunity attributable to the reactions of the cell-mediated immunity. Further, the delaminomycins of this invention are found to have an activity inhibitory to the proliferation of cancer cells for some kinds of cancer cells, and in this regard, they are useful as an anticancer agent. In summary, delaminomycins A, B, C, A2, B2 and C2 according to this invention are respectively useful for therapeutic treatments of bacterial infections by Gram-positive bacteria and also have their applications as an immunosuppressant or immunomodulator useful for the transplantation of organs and for treatments of auto-immune diseases. Besides, the delaminomycins have their applications as a useful anticancer agent against some kinds of cancers.

The biological activities of delaminomycins A, B and C according to the first aspect of this invention, as well as delaminomycins A2, B2 and C2 according to the second aspect of this invention are evaluated by the following Test Examples.

TEST EXAMPLE 1

Inhibitory activity of delaminomycins against the proliferation reaction of spleen cells caused by mitogen Compounds to be tested (delaminomycins) each were added at different concentrations to spleen cells of $CDF_1$ mouse suspended in RPMI 1640 medium (containing 10% fetal calf serum), and Concanavalin A as a mitogen was added thereto to give its concentration of 0.5 µg/ml. Then, the spleen cells were cultured under air at 37° C. for 72 hours and under conditions that air contained carbon dioxide at a concentration of 5%. At the 16th to 18th hour before the end of the cell cultivation, $^3$H-thymidine was added, and thereafter the proliferation of the cells was estimated in terms of the incorporation of $^3$H-thymidine into the cells. Further, the concentration of the test compound at which the cell proliferation was inhibited by 50%, namely the value of $IC_{50}$ of the test compound, was determined. The activity of the test compound inhibitory to the proliferation of spleen cells was evaluated in terms of the inhibition rate as calculated according to the following equation:

Inhibition rate (%)=100−(T/C×100)

wherein T denotes the quantity of incorporation of $^3$H-thymidine when the cells were treated with the test compound, but C denotes the quantity of incorporation of $^3$H-thymidine when the cells were not treated. The test results are shown in Table 1 below.

TABLE 1

Inhibitory activity on blastogenesis and proliferation of spleen lymphocyte caused by Con A

| Test Compound | Concentration of test compound (µg/ml) | Inhibition rate (%) | $IC_{50}$ (µg/ml) |
| --- | --- | --- | --- |
| Delaminomycin A | 100 | 88 | 17.5 |
| | 25 | 57 | |
| | 6.25 | 31 | |
| | 1.56 | 0 | |
| Delaminomycin B | 100 | 70 | 4.0 |
| | 25 | 69 | |
| | 6.25 | 77 | |
| | 1.56 | 0 | |
| | 0.39 | 0 | |
| Delaminomycin C | 100 | 76 | 1.0 |
| | 25 | 76 | |
| | 6.25 | 75 | |
| | 1.56 | 75 | |
| | 0.39 | 1 | |
| Delaminomycin A2 | 50 | 96.5 | 0.78 |
| | 12.5 | 95.1 | |
| | 3.1 | 76.3 | |
| | 0.78 | 50.5 | |
| | 0.20 | 1.5 | |
| Delaminomycin B2 | 50 | 96.7 | 0.85 |
| | 12.5 | 94.1 | |
| | 3.1 | 92.7 | |
| | 0.78 | 47.6 | |
| | 0.20 | 12.3 | |
| Delaminomycin C2 | 100 | 93 | 1.6 |
| | 25 | 85 | |
| | 6.25 | 84 | |
| | 1.56 | 49 | |
| | 0.39 | 0 | |
| | 0.1 | 0 | |

TEST EXAMPLE 2

Inhibitory activity of delaminomycins to the mixed lymphocyte culture reaction

As the stimulator cell for the mixed lymphocyte culture reaction, the spleen cells taken from WKY rat, which had been treated with 50 µg/ml of mitomycin C at 37° C. for 20 minutes, were used. As the responder cell, nylon wool-passed cells of spleen cells taken from Fischer F344 rat were used. These cells were mixed together and the mixed cells were cultured at 37° C. for 120 hours in RPMI 1640 medium (additionally containing 5% fetal calf serum) for the reaction in the presence or absence of a test compound (a delaminomycin) added at different concentrations while the cultivation of the cells was effected in air containing carbon dioxide at a concentration of 5%. At the 16th to 18th hour before the end of the reaction, $^3$H-thymidine was added to the cultures and the incorporation of $^3$H-thymidine into the cultured responder cell was measured by a liquid scintillation counter. The activity of test compound inhibitory to the mixed lymphocyte culture reaction was evaluated in terms of the inhibition rate [calculated by the equation: 100 −(T/C×100), %]. Further, the concentration of test compound at which the reaction was inhibited by 50%, namely the value of $IC_{50}$ of the test compound, was determined. The test results are shown in Table 2.

TABLE 2

Inhibitory activity on mixed lymphocyte culture reaction

| Test Compound | Concentration of test compound (μg/ml) | Inhibition rate (%) | $IC_{50}$ (μg/ml) |
|---|---|---|---|
| Delaminomycin A | 100 | 96.4 | 8.6 |
|  | 25 | 95.0 |  |
|  | 6.25 | 55.3 |  |
|  | 1.56 | 17.5 |  |
|  | 0.39 | 32.8 |  |
|  | 0.10 | 17.6 |  |
| Delaminomycin B | 100 | 93.2 | 1.1 |
|  | 25 | 95.0 |  |
|  | 6.25 | 95.1 |  |
|  | 1.56 | 58.4 |  |
|  | 0.39 | 27.9 |  |
|  | 0.10 | 12.1 |  |
| Delaminomycin C | 100 | 96.9 | 0.5 |
|  | 25 | 97.6 |  |
|  | 6.25 | 97.3 |  |
|  | 1.56 | 89.0 | 0.5 |
|  | 0.39 | 41.6 |  |
|  | 0.10 | 19.5 |  |
| Delaminomycin A2 | 100 | 56.0 | 13.9 |
|  | 25 | 94.0 |  |
|  | 6.25 | 5.0 |  |
|  | 1.56 | 0 |  |
|  | 0.39 | 5.0 |  |
|  | 0.10 | 16.0 |  |
| delaminomycin B2 | 50 | 96.7 | 8.6 |
|  | 12.5 | 94.1 |  |
|  | 3.1 | 92.7 | 8.6 |
|  | 0.78 | 47.6 |  |
|  | 0.20 | 12.3 |  |
|  | 0.05 | 0 |  |
| Delaminomycin C2 | 100 | 99.0 | 37.9 |
|  | 25 | 29.0 |  |
|  | 6.25 | −1.0 |  |
|  | 1.56 | 1.0 |  |
|  | 0.39 | −6.0 |  |
|  | 0.10 | −7.0 |  |

TEST EXAMPLE 3

Suppressive effect of delaminomycins on delayed-type hypersensitivity (DTH) in mouse $CDF_1$ mice were immunized by intravenously injecting sheep red blood cells ($10^5$ cells/mouse). On the 4th day after the immunization, sheep red blood cells ($10^8$ cells/mouse) were subcutaneously injected into the footpad of mice for the elicitation to cause a delayed-type hypersensitivity (DTH). Test compound was intraperitoneally administered to the mice once a day from the 0th day to 4th day after the immunization. On the 5th day after the elicitation the thickness of the mouse footpad was measured to estimate the suppressive effect of the test compound on the DTH response. The suppressive effect of the test compound was evaluated in terms of the inhibition rate (%) as calculated according to the following equation:

Inhibition rate (%)=100−(T/C×100)

wherein T denotes the thickness of the footpad when administering the test compound, but C denotes the thickness of the footpad when administering no test compound. The test results are shown in Table 3.

TABLE 3

Effect on delayed-type hypersensitivity in mouse

| Test Compound | Dose (μg/mouse) | Period of administration (day) | Inhibition rate (%) |
|---|---|---|---|
| Delaminomycin A | 1000 | 0–4th | 99.2 |
|  | 250 | 0–4th | 85.3 |
|  | 62.5 | 0–4th | 52.8 |
|  | 15.6 | 0–4th | 0.1 |
| Delaminomycin A2 | 1000 | 0–4th | 99.3 |
|  | 250 | 0–4th | 26.6 |
|  | 62.5 | 0–4th | 3.5 |
|  | 15.6 | 0–4th | 1.9 |
| Delaminomycin B2 | 1000 | 0–4th | 51.3 |
|  | 250 | 0–4th | 36.2 |
|  | 62.5 | 0–4th | 35.4 |
|  | 15.6 | 0–4th | −3.3 |

TEST EXAMPLE 4

Activity of delaminomycins inhibitory to proliferation of cancer cells

A variety of animal cancer cells and human cancer cells were cultured, and the inhibitory activity of delaminomycins of this invention against proliferation of these cancer cells was evaluated by measuring the concentration each of delaminomycins A, B, C, A2, B2 and C2 at which the proliferation of the cultured cancer cells was inhibited by 50%, that is, the value of $IC_{50}$ of a delaminomycin. The test results are shown in Table 4.

TABLE 4

Inhibitory activity of delaminomycins on proliferation of cancer cells: $IC_{50}$-value (μg/ml)

| Tested cancer cell | $IC_{50}$ of delaminomycins (μg/ml) | | | | | |
|---|---|---|---|---|---|---|
|  | A | B | C | A2 | B2 | C2 |
| Mouse leukemia L-1210 | >100 | 30.0 | 42.0 | 3.7 | 8.0 | 3.6 |
| Mouse leukemia $P388D_1$ | 14.0 | 13.3 | 3.1 | 10.0 | 12.1 | N.D |
| Mouse leukemia EL-4 | 17.9 | 11.1 | 1.9 | 4.1 | 6.8 | N.D |
| Mouse melanoma B-16 | 21.1 | >100 | 7.4 | 8.3 | 17.9 | N.D |
| Human Lymphoma Jurkat | 3.6 | 8.2 | 1.2 | 5.9 | 11.4 | N.D. |

Note:
N.D. means "not tested".

TEST EXAMPLE 5

Antibacterial activities

Delaminomycins A, B, C, A2, B2 and C2 according to this invention further have an antibacterial activity against a variety of bacteria. The minimum growth inhibitory concentrations (MIC) (μg/ml) of the novel antibiotics of this invention on various bacteria and fungi as measured by the agar plate dilution method are shown in Table 5a, Table 5b, Table 5c and Table 5d below.

TABLE 5a

| Tested microorganisms | Minimum growth inhibitory concentration of delaminomycins (μg/ml) | | |
|---|---|---|---|
| | A | B | C |
| Staphylococcus aureus FDA209P | 12.5 | 6.25 | 3.12 |
| Staphylococcus aureus Smith | 25 | 6.25 | 3.12 |
| Staphylococcus aureus MS9610 | 25 | 6.25 | 3.12 |
| Staphylococcus aureus No. 5 (MRSA) | 25 | 6.25 | 3.12 |
| Staphylococcus aureus No. 17 (MRSA) | 25 | 6.25 | 3.12 |
| Micrococcus luteus FDA16 | 6.25 | 3.12 | 1.56 |
| Micrococcus luteus IFO3333 | 6.25 | 3.12 | 1.56 |
| Micrococcus luteus PCI1001 | 100 | 6.25 | 1.56 |
| Bacillus anthracis | 3.12 | 1.56 | <0.78 |
| Bacillus subtilis NRRL B-558 | 6.25 | 6.25 | 3.12 |
| Bacillus subtilis PCI1219 | 6.25 | 6.25 | 3.12 |
| Bacillus cereus ATCC10702 | 6.25 | 3.12 | 1.56 |
| Corynebacterium bovis 1810 | 3.12 | 6.25 | 3.12 |
| Escherichia coli NIHJ | >100 | >100 | >100 |
| Escherichia coli K-12 | >100 | >100 | >100 |
| Escherichia coli K-12 ML1629 | >100 | >100 | >100 |
| Escherichia coli BEM11 | >100 | >100 | >100 |
| Escherichia coli BE1121 | >100 | >100 | >100 |
| Escherichia coli BE1186 | >100 | >100 | >100 |
| Shigella dysenteriae JS11910 | >100 | >100 | >100 |
| Shigella flexneri 4b JS11811 | >100 | >100 | >100 |
| Shigella sonnei JS11746 | >100 | >100 | >100 |
| Salmonella typhi T-63 | >100 | >100 | >100 |
| Salmonella enteritidis 1891 | >100 | >100 | >100 |
| Proteus vulgaris OX19 | >100 | >100 | >100 |
| Proteus mirabilis IFM OM-9 | >100 | >100 | >100 |
| Proteus rettgeri GN311 | >100 | >100 | >100 |
| Proteus rettgeri GN466 | >100 | >100 | >100 |
| Serratia marcescens | >100 | >100 | >100 |
| Pseudomonas aeruginosa A3 | >50 | >50 | >50 |
| Pseudomonas aeruginosa GN315 | >100 | >100 | >100 |
| Klebsiella pneumoniae PC1602 | >100 | >100 | >100 |
| Mycobacterium smegmatis ATCC607 | >100 | >100 | >100 |

Note:
Evaluated after culturing at 37° C. for 18 hours in Muller Hinton agar medium (produced by Difco Co.).

TABLE 5b

| Tested microorganisms | Minimum growth inhibitory concentration of delaminomycins (μg/ml) | | |
|---|---|---|---|
| | A | B | C |
| Candida tropicalis F-1 | >100 | >100 | >100 |
| Candida pseudotropicalis F-2 | >100 | >100 | >100 |
| Candida albicans 3147 | >100 | >100 | >100 |
| Candida Yu-1200 | >100 | >100 | >100 |
| Candida krusei F-5 | >100 | >100 | >100 |
| Saccharomyces cerevisiae F-7 | >100 | >100 | >100 |
| Cryptococcus neoformans F-10 | >100 | >100 | >100 |
| Cochliobolus miyabeanus | >100 | >100 | >100 |
| Piricularia oryzae | >100 | >100 | >100 |
| Pellicularia sasakii | >100 | >50 | >50 |
| Xanthomonas citri | >100 | >100 | >100 |
| Xanthomonas oryzae | >100 | >100 | >100 |
| Aspergillus niger F-16 | >100 | >100 | >100 |
| Trichophyton asteroides 429 | >100 | >100 | >100 |
| Trichophyton mentagrophytes F-15 (833) | >100 | >100 | >100 |

Note:
Evaluated after culturing at 27° C. for 42 hours in nutrient agar medium containing glucose.

TABLE 5c

| Tested microorganisms | Minimum growth inhibitory concentration of delaminomycins (μg/ml) | | |
|---|---|---|---|
| | A2 | B2 | C2 |
| Staphylococcus aureus FDA209P | 12.5 | 50 | 100 |
| Staphylococcus aureus Smith | 12.5 | >100 | >100 |
| Staphylococcus aureus MS9610 | 12.5 | >100 | >100 |
| Staphylococcus aureus No. 5 (MRSA) | 12.5 | >100 | >100 |
| Staphylococcus aureus No. 17 (MRSA) | 12.5 | >100 | >100 |
| Micrococcus luteus FDA16 | 6.25 | 12.5 | >100 |
| Micrococcus luteus IFO3333 | 6.25 | 12.5 | 100 |
| Micrococcus luteus PCI1001 | 12.5 | >100 | >100 |
| Bacillus anthracis | 6.25 | 25 | 100 |
| Bacillus subtilis NRRL B-558 | 6.25 | >100 | >100 |
| Bacillus subtilis PCI1219 | 12.5 | >100 | >100 |
| Bacillus cereus ATCC10702 | 6.25 | 50 | >100 |
| Corynebacterium bovis 1810 | 12.5 | 100 | >100 |
| Escherichia coli NIHJ | >100 | >100 | >100 |
| Escherichia coli K-12 | >100 | >100 | >100 |
| Escherichia coli K-12 ML1629 | >100 | >100 | >100 |
| Escherichia coli BEM11 | >100 | >100 | >100 |
| Escherichia coli BE1121 | >100 | >100 | >100 |
| Escherichia coli BE1186 | >100 | >100 | >100 |
| Shigella dysenteriae JS11910 | >100 | >100 | >100 |
| Shigella flexneri 4b JS11811 | >100 | >100 | >100 |
| Shigella sonnei JS11746 | >100 | >100 | >100 |
| Salmonella typhi T-63 | >100 | >100 | >100 |
| Salmonella enteritidis 1891 | >100 | >100 | >100 |
| Proteus vulgaris OX19 | >100 | >100 | >100 |
| Proteus mirabilis IFM OM-9 | >100 | >100 | >100 |
| Proteus rettgeri GN311 | >100 | >100 | >100 |
| Proteus rettgeri GN466 | >100 | >100 | >100 |
| Serratia marcescens | >100 | >100 | >100 |
| Pseudomonas aeruginosa A3 | >50 | >50 | >50 |
| Pseudomonas aeruginosa GN315 | >100 | >100 | >100 |
| Klebsiella pneumoniae PC1602 | >100 | >100 | >100 |
| Mycobacterium smegmatis ATCC607 | 12.5 | >100 | >100 |

Note:
Evaluated after culturing at 37° C. for 18 hours in Muller Hinton agar medium (produced by Difco Co.).

TABLE 5d

| Tested microorganisms | Minimum growth inhibitory concentration of delaminomycins (μg/ml) | |
|---|---|---|
| | A2 | B2 |
| Candida tropicalis F-1 | >100 | >100 |
| Candida pseudotropicalis F-2 | >100 | >100 |
| Candida albicans 3147 | >100 | >100 |
| Candida Yu-1200 | >100 | >100 |
| Candida krusei F-5 | >100 | >100 |
| Saccharomyces cerevisiae F-7 | >100 | >100 |
| Cryptococcus neoformans F-10 | >100 | >100 |
| Cochliobolus miyabeanus | >100 | >100 |
| Piricularia oryzae | >100 | >100 |
| Pellicularia sasakii | >50 | >50 |
| Xanthomonas citri | >100 | >100 |
| Xanthomonas oryzae | >100 | >100 |
| Aspergillus niger F-16 | >100 | >100 |
| Trichophyton asteroides 429 | >100 | >100 |
| Trichophyton mentagrophytes F-15 (833) | >100 | >100 |

Note:
Evaluated after culturing at 27° C. for 42 hours in nutrient agar medium containing glucose.

Further, according to a third aspect of this invention, there is provided a process for the production of new antibiotics having an immunosuppressive activity, delaminocycin A and/or delaminomycin B and/or delaminmycin C, characterized in that the process comprises cultivating a microorganism which produces delaminomycin A, delaminomycin B and delaminomycin C and belongs to the genus *Streptomyces,* and recovering delaminomycin A and/or delaminomycin B and/or delaminomycin C from the resulting culture.

The microorganism which produces delaminmycins A, B and C and is to be used in the above process of this invention may be any strain so far as it belongs to the genus *Streptomyces* and has an ability to produce at least one of delaminomycins A, B and C, and it is not limited to a specific strain. An example of the microorganism capable of producing delaminomycins A, B and C, which may be used in this invention, is a strain of actinomycetes which was isolated from a soil sample collected in Ohtsuki City, Yamanashi Prefecture, Japan, in January 1990, to which a strain number of MJ202-72F3 had been allotted.

Now, the microbiological properties of the strain MJ202-72F3 are described.

1. Morphology

The strain MJ202-72F3 extends relatively long aerial hyphae from branched vegitative hyphae, and the aerial hyphae have their ends in the form of spiral with 5–6 revolutions. Neither whirl nor sporangium is observed. On the end of the aerial hyphae, a chain of 50 or more spores is found, and each spore has dimensions of about 0.5–0.7× 0.8–1.2 microns. The surface of the spore is spiny or warty.

2. Conditions of the growth in various media

Descriptions of colors are given with the color standards shown in brackets [] which are based on the Color Harmony Manual of Container Corporation of America.

(1) Sucrose-nitrate agar medium (cultured at 30° C.)
   A growth of colorless to pale yellow color is observed with a partial formation of light gray [2fe, Covert Gray] aerial hyphae. No soluble pigment is produced.

(2) Glucose-asparagine agar medium (cultured at 30° C.)
   A growth of pale yellow color is observed without formation of aerial hyphae. No soluble pigment is produced.

(3) Glycerin-asparagine agar medium (medium ISP No. 5, cultured at 30° C.).
   A growth of pale yellow [2gc, Bamboo] color is observed with thin formation of white aerial hyphae. No soluble pigment is produced.

(4) Starch-inorganic salt agar medium (medium ISP No. 4, cultured at 30° C.)
   A growth of colorless to pale yellow color is observed with a scant formation of light gray [3fe, Silver Gray] aerial hyphae. No soluble pigment is produced.

(5) Tyrosine agar medium (medium ISP No. 7, cultured at 30° C.)
   A growth of pale yellow [2gc, Bamboo] color is observed with thin formation of white aerial hyphae. No soluble pigment is produced.

(6) Nutrient agar medium (cultured at 30° C.)
   A growth of pale yellow color is observed without formation of aerial hyphae. No soluble pigment is produced.

(7) Yeast extract-malt agar medium (medium ISP No. 2, cultured at 30° C.)
   A growth of pale yellow [1½ic, Lt Antique Gold] color is observed with a partial formation of light gray [f,~2fe, Covert Gray] aerial hyphae. No soluble pigment is produced.

(8) Oatmeal agar medium (medium ISP No. 3, cultured at 30° C.)
   A growth of pale yellow color is observed with a scant formation of white aerial hyphae. No soluble pigment is produced.

(9) Glycerin-nitrate agar medium (cultured at 30° C.)
   A growth of colorless to pale yellow color is observed without formation of aerial hyphae. No soluble pigment is produced.

(10) Starch agar medium (cultured at 30° C.)
   A growth of no color is observed without formation of aerial hyphae. No soluble pigment is produced.

(11) Calcium malate agar medium (cultured at 30° C.)
   A growth of no color is observed without formation of aerial hyphae. No soluble pigment is produced.

(12) Cellulose (synthetic solution containing filter paper pieces, cultured at 30° C.)
   No growth is observed after culturing for 40 days

(13) Gelatin stab culture
   In a 15% simple gelatin medium (cultured at 20° C.), a growth of pale yellow color is observed with a scant formation of brownish white aerial hyphae, and without production of soluble pigment. In a glucose-peptone-gelatin medium (cultured at 27° C.), a growth of pale yellow color is observed without formation of aerial hyphae, but with production of slightly brownish-colored soluble pigment.

(14) Skimmed milk (cultured at 30° C. and at 37° C.)
   When cultured at 30° C., a growth of pale yellow color is observed without formation of aerial hyphae and without production of soluble pigment. When cultured at 37° C., the growth is very poor, and a slight growth of light yellow color is observed without formation of aerial hyphae and without production of soluble pigment.

3. Physiological characteristics (1) Temperature range for growth
   When tested in a glucose-asparagine-agar medium (comprising 1.0% glucose, 0.05% L-asparagine, 0.05% dipotassium phosphate, 3.0% agar string, pH 7.0) at temperatures of 20° C., 24° C., 27° C., 30° C., 37° C. and 50° C., the growth is developed at any of these temperatures except for 50° C., provided that the growth is very poor at 37° C. The optimum temperature for growth is considered to be about 27° C. to 30° C.

(2) Liquefaction of gelatin (in a 15% simple gelatin medium, cultured at 20° C.; and in glucose-peptone-gelatin medium, cultured at 27° C.)
   In any of these media, no liquefaction of gelatin is observed in a culturing period of 21 days.

(3) Hydrolysis of starch (in a starch-inorganic salt-agar medium and starch-agar medium; both cultured at 30° C.)

No hydrolysis of starch is observed in any of these media.

(4) Coagulation and peptonization of skimmed milk (skimmed milk, cultured at 30° C. and at 37° C.)

When cultured at 30° C., the peptonization starts without coagulation of the milk from about the 21st day after the start of the culturing, but the peptonizing action is very weak. When cultured at 37° C., the growth is very poor, and the actions of coagulation and peptonization are not observed.

(5) Formation of melanoid pigment (in trypton-yeast-broth, medium ISP No. 1; peptone-yeast-iron agar medium, medium ISP No. 6; thyrosine-agar medium, medium ISP No. 7; all cultured at 30° C.).

Negative in all the media.

(6) Utilization of carbon sources (in Pridham-Gottlieb agar medium, medium ISP No. 9; cultured at 30° C.).

The strain grows with utilizing D-glucose and inositol, but does not utilize sucrose, D-mannitol and lactose. Utilization of D-xylose and D-fructose is doubtful. It is probable that L-arabinose, rhamnose and raffinose are not utilized.

(7) Dissolution of calcium malate (in calcium malate-agar medium, cultured at 30° C.)

From about the 7th day after the start of culturing, dissolution of calcium malate is observed, and the degree of dissolution is moderate.

(8) Reduction of nitrate (in an aqueous peptone containing 0.1% potassium nitrate, medium ISP No. 8, cultured at 30° C.)

Negative.

(9) Degradation of cellulose (in a synthetic solution containing filter paper pieces, cultured at 30° C.)

Upon culturing for 40 days, neither growth nor degradation of cellulose is observed.

Summarizing the morphological properties as above-mentioned, the strain MJ202-72F3 extends from branched vegitative hyphae the aerial hyphae having spiral with 5–6 revolutions, and neither whirl nor sporangium is formed. The end of the aerial hyphae has a chain of 50 or more spores, and the surface of the spore is spiny or warty. The growths on various media are of no color to pale yellow color, and the formation of aerial hyphae is poor, although a partial formation of aerial hyphae of light gray color is observed in a few media. No soluble pigment is produced. The optimum temperature for growth is about 27° C. to 30° C. The formation of melanoid pigment is negative, no hydrolysis of starch is observed, and the ability to degrade protein is weak.

The 2,6-diaminopimelic acid present in the cell wall of the strain has LL-type.

Based on these characteristic properties, the strain MJ202-72F3 is considered to belong to the genus *Streptomyces*. By searching known strains of the genus *Streptomyces*, *Streptomyces albulus* ("International Journal of Systematic Bacteriology", Vol 22 page 271, 1972; ibid Vol 30, page 371, 1980) and *Streptomyces natalensis* ("International Journal of Systematic Bacteriology", Vol 22 page 323, 1972) can be mentioned as similar strains. At that stage, the strain MJ202-72F3 was designated as *Streptomyces* sp. MJ202-72F3.

The inventors applied to Fermentation Research Institute, Agency of Industrial Science & Technology, Japan (at Tsukuba-city, Ibaragi Prefecture) for deposit of the strain MJ202-72F3, and it was deposited under the accession number FERM-P 12674 on 24 Dec., 1991.

Further, we, the present inventors, actually studied on the comparisons between MJ202-72F3 strain and the above-mentioned two strains, namely *Streptomyces albulus* IMC S-0802 (ISP 5492), and *Streptomyces natalensis* IMC S-0687 (ISP 5357). As a result, the strain MJ202-72F3 was found to be somewhat different from both the above-mentioned two strains in respect of liquefaction of gelatin, coagulation and peptonization of milk, and hydrolysis of starch. It is not considered, however, that the difference in such properties as above is substantial, because these properties are apt to vary. Further the strain MJ202-72F3 appeared to be more resemble to *Streptomyces albulus* in respect of the color of aerial hyphae, utilization of carbon sources and others. Thus, we have identified the strain MJ202-72F3 as *Streptomyces albulus* MJ202-72F3 strain.

At present, the deposit of the strain MJ202-72F3 was transferred under the provisions of Budapest Treaty, and this strain is deposited with the above-mentioned Fermentation Research Institute, Agency of Industrial Science & Technology, Japan (now renamed "National Institute of Bioscience & Human-Technology" under Deposit number: FERM BP-4079.

BEST MODE FOR CARRYING OUT THE INVENTION

Now, the production of antibiotics, delaminomycins A, B and C by the process of the third aspect of this invention is explained.

New antibiotics, delaminomycins A, B and C may be produced by culturing a microorganism belonging to the genus *Streptomyces* and capable of producing delaminomycins A, B and C in an appropriate culture medium, preferably under an aerobic condition, to produce and accumulate the objective antibiotics in the medium, and then recovering the objective antibiotics from the resulting culture.

The culture medium may be one containing any nutrients which the microorganism capable of producing delaminomycins A, B and C can utilize. More specifically speaking, glucose, inositol, maltose, fatty oils and the like can be used as the carbon sources. Ogranic matters such as soybean flour, cotton seed meal, dried yeast extract, polypeptone, corn steep liquor and the like, as well as inorganic matters including ammonium salts and nitrates such as ammonium sulfate, sodium nitrate, ammonium chloride and the like can be used as the nitrogen sources. If desired, inorganic salts such as sodium chloride, potassium chloride, calcium carbonate, phosphoric acid salts, heavy metal salts and the like can be added to the medium. In order to prevent the foaming in the process of fermentation, an appropriate antifoaming agent such as silicone-type antifoaming agent may be added in the usual manner.

As the method of cultivation, any methods conventionally utilized for cultivating microorganisms to produce physiologically active antibiotics may be employed, and among them, aerobic submurged cultivation method is particularly suitable. The suitable temperature for the cultivation is usually 20°–37° C., and preferably 27°–30° C. Under these conditions, the production of delaminomycins A, B and C reaches a maximum value in 5–7 days, both in the shaking cultivation method and in the cultivation method under aeration and agitation. Thus, there can be obtained a culture in which delaminomycins A, B and C are produced and accumulated.

In the culture, delaminomycins A, B and C are present in the cultured mycellia or cells and in the culture broth filtrate, and are in a larger quantity in the cells. For recovering delaminomycins A, B and C from such culture, any methods may be adopted so far as they are reasonable for and fit the purpose intended. One of these methods is that based on the principle of extraction. Illustratively, it includes such method in which delaminomycins A, B and C contained in the culture broth filtrate are extracted with a water-immiscible organic solvent such as butyl acetate, n-butanol and the like. It also includes such method in which delaminomycins A, B and C present in the cultured cells are recovered by collecting the cells by filtration, centrifugation and the like, followed by extracting the collected cell mass with methanol, ethanol, acetone and the like. It is also possible to subject the whole culture directly to the above-mentioned operation of the extraction without separating the cells from the culture. A counter-current partition method using appropriate solvents can be regarded as a sort of the methods for the extraction. For example, centrifugal partition chromatography, (CPC, a product of Sanki Engineering Co.) (note: CPC is a tradename) is adoptable.

One of other methods for recovering delaminomycins A, B and C from the culture is based on the principle of adsorption. For example, either the culture broth filtrate or an extract solution having been obtained by the above-mentioned extraction procedure may be subjected to adsorption with an appropriate adsorbent or a gel filtration agent so as to adsorb the desired antibiotics thereon, for example, by means of a column chromatography using silica gel, Sephadex LH-20 (a product of Pharmacia Co.), Toyopearl HW-40 (a product of Toso Co.), Diaion HP-20 (a product of Mitsubishi Chemical Co.) etc., or a high performance liquid chromatography using Nucleosil 5 $C_{18}$ (a product of Nagel Co., Germany) etc., or other methods, and thereafter the adsorbed antibiotics are eluted so that delaminomycins A, B and C, either alone or in the form of a mixture, may be separated. When the resulting solution containing delaminomaycin A and/or delaminomycin B and/or delaminomycin C so obtained is then concentrated to dryness under a reduced pressure, a crude product of delaminomycin A and/or delaminomycin B and/or delaminomycin C can be afforded.

In order to purify further the crude product of delaminomycin A and/or delaminomycin B and/or delaminomycin C thus obtained, the above-mentioned extraction and adsorption methods may be repeated as required, and made in combination as required. For example, there may be employed an appropriate combination of a column chromatography using an adsorbent or a gel filtration agent such as Diaion HP-20 or Sephadex LH-20 (trade name) etc., with a centrifugal liquid-liquid partition chromatography using CPC, a chromatography in a descending mode on silica gel, and a high performance liquid chromatography using Nucleosil 5 $C_{18}$ and the like.

We, the present inventors, further proceeded our studies. As a result, we have found that antibiotic, delaminomycin A2 or B2 or C2 represented by the above-mentioned general formula (II) can be produced by dissolving the antibiotic, delaminomycin A, B or C represented by the above-mentioned general formula (I) or (I') in an anhydrous organic solvent and stirring the resulting solution with an inorganic acid, whereby the starting delaminomycin can undergo a ring-closure reaction with accompanying dehydration, to give delaminomycin A2 or B2 or C2.

According to the fourth aspect of this invention, therefore, there is provided a process for the production of the new antibiotic, delaminomycin A2, delaminomycin B2 or delaminomycin C2, characterized in that the process comprises subjecting delaminomycin A, delaminomycin B or delaminomycin C to a ring-closure reaction with accompanying dehydration.

In carrying out the process according to the fourth aspect of this invention, the starting delaminomycin A or B or C may be dissolved in an anhydrous organic solvent, for example, methanol, ethanol, n-butanol or acetone, then an inorganic acid such as hydrochloric acid or sulfuric acid is added to the resulting solution, and the resultant mixture may undergo the reaction at room temperature or under heating. The delaminomycin A2 or B2 or C2 as desired may be recovered from the reaction solution so formed, by distilling off the solvent used and then subjecting the residue to various chromatographic treatments.

Delaminomycin A or B or C of the general formula (I) or (I') or a salt thereof according to the first aspect of this invention, or delaminomycin A2 or B2 or C2 of general formula (II) according to the second aspect of this invention, when utilized as immunosuppressant or other medicinal agents, may be formulated into pharmaceutical compositions by blending the active ingredient with a pharmaceutically acceptable and conventional solid or liquid carrier or carriers.

According to the fifth aspect of this invention, therefore, there is provided a pharmaceutical composition comprising as an active ingredient at least one antibiotic selected from the group consisting of delaminomycin A, delaminomycin B, delaminomycin C, delaminomycin A2, delaminomycin B2 and delaminomycin C2, or a pharmaceutically acceptable salt of said antibiotic, and further comprising a pharmaceutically acceptable solid or liquid carrier as mixed with the active ingredient.

In cases where one or more delaminomycins of the general formula (I) or (I') or of the general formula (II) according to this invention are used as an immunosuppressant or immunomodulator or other medicinal agent, they can generally be administered orally or parenterally.

Delaminomycin A has a very low toxicity, as it shows an $LD_{50}$ value of more than 500 mg/kg when administered intraperitoneally to ICR mice.

The active ingredient compound of the above composition according to this invention, i.e. delaminomycin A, B, C or their salts, or delaminomycin A2, B2 or C2 may be administered by itself or in the form of a preparation wherein the delaminomycin has been blended with an excipient or carrier, such as injections, oral preparations, suppositories and the like. Excipients and carriers may be selected from those pharmaceutically acceptable ones, and the nature and composition of the excipient or carrier may vary depending upon the route and manner of administration. For example, there may be used as a liquid carrier water, alcohol, an animal or vegitable oil such as soybean oil, sesame oil or mineral oil, or a synthetic oil. Usable solid carriers include, for example, a sugar such as maltose, sucrose and the like, an amino acid such as lysine, a cellulose derivative such as hydroxypropyl cellulose and the like, a polysaccharide such as cyclodextrin, a salt of an organic acid such as magnesium stearate and the like.

In cases where injections are to be prepared, it is generally desirable to use physiological saline, various buffered solutions, an aqueous solution of a sugar such as glucose, inositol or mannitol, or a glycol such as ethylene glycol or polyethylene glycol. It is also feasible to formulate a lyophilized preparation containing the active ingredient in combination with an excipient or excipients, e.g. a sugar such as inositol, mannitol, glucose, mannose, maltose, sucrose and the like, or an amino acid such as phenyl alanine and the like. Upon administration, such lyophilized preparation may be dissolved in a suitable solvent for injection, for example, an intravenously administrable liquid such as sterilized water, physiological saline, an aqueous solution of glucose, an aqueous solution of electrolytes, an aqueous solution of amino acids.

The proportion of delaminomycin compound(s) present in the formulated composition may vary from one type to another type of the preparation, but usually may be 0.1–100% by weight, preferably 1–90% by weight. In cases of preparations for injection, for example, it is usually desirable to contain 0.1–5% by weight of the delaminomycin compound therein. In cases of oral preparations, they are used in the form of tablets, capsules, a powder, granules, a dry syrup, liquid, a syrup and the like in combination with the above-mentioned solid carriers or liquid carriers. In capsules, tablets, granules or a powder, the proportion of the delaminomycin compound present therein may usually be 3–100% by weight, preferably 5–90% by weight, with the balance being formed of the carrier(s).

The dosage of delaminomycins or their salts according to this invention may be determined taking account of the age, body weight, symptom of patients and therapeutic purpose as intended. As a generic guide, the effective dosage is in the range of 1–100 mg/kg/day for parenteral administration and in the range of 5–500 mg/kg/day for oral administration. This dosage can be administered either continuously or intermittently so long as the total dosage does not exceed a specific level that was decided in view of results of animal tests and various circumstances.

The total dosage given by the parenteral administration may, of course, vary according to circumstances depending upon the way of administration, conditions of the patient under treatment, for example, the age, body weight, sex, foods, other drugs concurrently administered, and the like. The suitable dosage and administration frequency of the delaminomycin of this invention under given conditions must be determined by an expert physician in the light of the above-mentioned guidelines. These requirements for administration should also apply to the oral administration of the same.

Delaminomycins A, B and C represented by the general formula (I) or (I') according to the first aspect of this invention, as well as delaminomycins A2, B2 and C2 represented by the general formula (II) according to the second aspect of this invention are of such nature that they were barely soluble in water and that they were hardly absorbed into the digestive tracts when orally administered. Thus, we have continued our investigations with the intention of synthesizing such new derivatives of the delaminomycins which have some advantageous properties over the delaminomycins such that the new derivatives are much easily soluble in water and much easily absorbed into the digestive tracts through oral administration, and also they can be easily formulated into injection preparations and can achieve an improved efficiency on oral absorption thereof.

Accordingly, we have synthesized a variety of derivatives of delaminomycins which have a higher solubility in water than the delaminomycins themselves, and we have examined them. As a result, we have succeeded in the synthesis of novel sulfuric acid esters of delaminomycin A2, delaminomycin B2, and delaminomycin C2 represented by the following general formula (III)

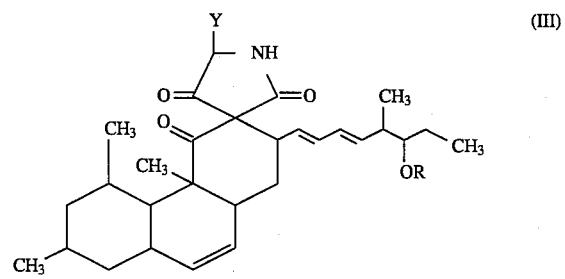

wherein R stands for a sulfuric acid residue —$SO_3H$ or a pharmaceutically acceptable salt of the sulfuric acid residue, and Y is a hydroxyl group for delaminomycin A2, a methoxy group for delaminomycin B2 and a hydrogen atom for delaminomycin C2, or a pharmaceutically acceptable salt of said sulfuric acid esters. And, we have found that these novel derivatives of the formula (III) have high solubilities in water and improved absorption efficiencies through oral administration thereof and also have an immunosuppressive activities.

According to the sixth aspect of this invention, therefore, there is provided delaminomycin A2 sulfuric acid ester, delaminomycin B2 sulfuric acid ester or delaminomycin C2 sulfuric acid ester represented by the above-shown general formula (III), or a pharmaceutically acceptable salt of said sulfuric acid esters.

The production of the compounds of the general formula (III) according to this invention may be effected, for example, by the following method. That is, delaminomycin A2 or B2 or C2 is reacted with a sulfating reagent in an aprotic solvent. The amount of the sulfating reagent used may usually be equimolar or more in respect of the starting delaminomycin A2, B2 or C2. The sulfating reagent may typically be sulfuric acid anhydride-pyridine complex, chlorosulfonic acid and the like. The aprotic solvent for the esterification may preferably be N, N'-dimethylformamide, pyridine and the like.

As a neutralizing agent to be added during the reaction, there may be used an organic base such as pyridine, triethylamine and the like, and an inorganic base such as calcium hydroxide, sodium hydrogen carbonate, potassium carbonate and the like. The reaction may usually be carried out at a temperature below the boiling point of the solvent used and preferably at a temperature in the range of about −20° C. – room temperatures.

The compound of the general formula (III) in the sulfuric acid ester form may be isolated from the reaction solution containing said compound therein, for example in the following manner. Thus, the reaction solution containing said sulfuric acid ester compound may be treated by extracting the compound with water and ethyl acetate or dichloromethane therefrom. The extract layer containing the desired compound of the general formula (III) is then concentrated and the concentrated residue may be purified if necessary, by a column chromatography and the like and then the compound of general formula (III) according to this invention can be isolated in a conventional manner.

The sulfuric acid ester derivative of general formula (III) according to the sixth aspect of this invention can form a salt with a non-toxic metal, for example, an alkali metal such as sodium or potassium, or an organic base such as triethylamine by a usual reaction method.

The compound of the general formula (III) obtained according to the sixth aspect of this invention, particularly in its sodium salt form, has significantly enhanced solubility in water, as compared to that of the corresponding compound of the non-sulfuric acid ester type, and it is easily soluble in water.

(a') Sodium salt of the sulfuric acid ester of delaminomycin A2 according to the sixth aspect of this invention, which is a compound of the general formula (III) where Y is a hydroxyl group, has the following physico-chemical properties:

(1) Thin layer chromatography (using Silica Gel 60F$_{254}$ Art. 5554; a product of Merck Co.): Rf 0.65 (when developed with a developing solvent comprising 2-propanol-aqueous ammonia-water, 9:1:2). Rf 0.15 (when developed with a developing solvent comprising chloroform-methanol-aqueous ammonia, 40:10:1).

(2) Color reaction: positive to vanillin-sulfuric acid.

(3) Color and appearance of the substance: colorless to white, solid.

(4) Empirical formula: $C_{29}H_{40}O_8NSNa$ (5) Elementary analysis: for $C_{29}H_{40}O_8NSNa \cdot 2H_2O$

|  | C | H | O | N | S | Na |
|---|---|---|---|---|---|---|
| Found (%): | 55.83 | 6.81 | N.D. | 1.94 | 5.06 | N.D. |
| Calculated (%): | 56.03 | 7.13 | 25.73 | 2.25 | 5.15 | 3.70 |

(N.D. represents "not determined".)

(6) Molecular weight: 585

(7) High resolution FAB (Fast Atom Bombardment) mass spectrum (negative ion mode): for $C_{29}H_{40}O_8NSNa$ [(M−Na)$^-$, m/z ]

Found: 562.2471

Calculated: 562.2475

(8) Ultraviolet absorption spectrum: the following absorption peak is shown when measured in a methanolic solution. $\lambda_{max}^{MeOH}$ nm ($E_{1\ cm}^{1\%}$) : 232 (492)

(9) Infrared absorption spectrum (KBr method): as shown in FIG. 7 of the accompanying drawings. $v_{max}^{KBr}$ : 3430, 2950, 2900, 1785, 1710, 1680, 1250, 1210, 1060, 940 cm$^{-1}$

(10) $^1$H-NMR spectrum (400 MHz): δ 8.0(1H, m), 6.0(2H, m), 5.4~5.6(4H, m), 5.0(1H, s), 4.2(1H, m), 3.0(3H, m), 2.3~2.6(3H, m), 2.0(2H, m), 1.6~1.8(4H, m), 1.4~1.5(4H, m), 1.5(3H, d), 0.9~1.0(9H, m), 0.7(3H, d)

The $^1$H-NMR spectrum is measured in deutero-chloroform using TMS (0 ppm) as a standard substance.

(11) $^{13}$C-NMR spectrum (100 MHz): δ 212.1(s), 202.4(s), 169.3(s), 136.4(d), 134.1(d), 130.7(d), 129.9(d), 128.3(d), 126.8(d), 85.9(d), 78.6(d), 71.0(s), 54.1(s), 47.2(t), 46.0(d), 44.4(d), 43.8(d), 42.4(t), 40.4(d), 39.3(d), 35.5(d), 33.2(d), 32.0(t), 22.1(t,q), 19.5(q), 17.3(q), 17.1(q), 9.9(q)

The $^{13}$C-NMR spectrum is measured in deutero-chloroform using chloroform (77.00 ppm) as a standard substance.

(12) Solubility: soluble in water, methanol, ethyl acetate, chloroform but slightly soluble or insoluble in ethyl ether and n-hexane.

(b') Sodium salt of the sulfuric acid ester of delaminomycin B2 according to the sixth aspect of this invention, which is a compound of the general formula (III) where Y is a methoxy group, has the following physico-chemical properties:

(1) Thin-layer chromatography (on Silica Gel 60F$_{254}$ Art. 5554; a product of Merck Co.): Rf 0.19 (when developed with a developing solvent comprising chloroform-methanol-aqueous ammonia, 40:10:1).

(2) Color reaction: positive to vanillin-sulfuric acid.

(3) Color and appearance of the substance: colorless to white, solid.

(4) Empirical formula: $C_{30}H_{42}O_8NSNa$ (5) Molecular weight: 599

(6) FAB (Fast Atom Bombardment) mass spectrum: m/z 576 (M−Na)$^-$ (7) Ultraviolet absorption spectrum: the following absorption peak is shown when measured in a methanolic solution. $\lambda_{max}^{MeOH}$ nm ($E_{1\ cm}^{1\%}$) : 232 (470)

(8) Infrared absorption spectrum (KBr method): $v_{max}^{KBr}$ : 3450, 2900, 1780, 1710, 1200~1250, 940 cm$^{-1}$ (9) $^{13}$C-NMR spectrum (100 MHz): δ 53.0 (q), 85.9 (d)

(10) Solubility: soluble in water, methanol, ethyl acetate, chloroform but slightly soluble or insoluble in ethyl ether and n-hexane.

(c') Sodium salt of the sulfuric acid ester of delaminomycin C2 according to the sixth aspect of this invention, which is a compound of the general formula (III) where Y is a hydrogen atom, has the following physico-chemical properties:

(1) Thin layer chromatography (on Silica Gel 60F$_{254}$ Art. 5554; a product of Merck Co.) Rf 0.27 (when developed with a developing solvent comprising chloroform-methanol-aqueous ammonia, 40:10:1).

(2) Color reaction: positive to vanillin-sulfuric acid.

(3) Color and appearance of the substance: colorless to white, solid.

(4) Empirical formula: $C_{29}H_{40}O_7NSNa$ (5) Molecular weight: 569

(6) FAB (Fast Atom Bombardment) mass spectrum: m/z 546 (M−Na)$^-$ (7) Ultraviolet absorption spectrum: the following absorption peak is shown when measured in a methanolic solution. $\lambda_{max}^{MeOH}$ nm ($E_{1\ cm}^{1\%}$) : 232 (502)

(8) Infrared absorption spectrum (KBr method): $v_{max}^{KBr}$ : 3430, 2950, 2910, 1790, 1710, 1240, 1210, 1040 cm$^{-1}$ (9) $^1$H-NMR spectrum (400 MHz): δ 3.9 (1H, d), 3.7 (1H, d)

The $^1$H-NMR spectrum is measured in deutero-chloroform using TMS (0 ppm) as a standard substance.

(10) $^{13}$C-NMR spectrum (100 MHz): δ 50.9 (t), 86.1 (d)

The $^{13}$C-NMR spectrum is measured in deutero-chloroform using chloroform (77.00 ppm) as a standard substance.

(11) Solubility: soluble in water, methanol, ethyl acetate, chloroform but slightly soluble or insoluble in ethyl ether and n-hexane.

The following Test Example is given to demonstrate that sodium salts of the compounds having the general formula (III) according to the sixth aspect of this invention exhibit a suppressive effect on the delayed-type hypersensitivity (DTH) in mouse and thus possess an immunosuppressive activity.

TEST EXAMPLE 6

CDF$_1$ mice were immunized by intravenously injecting sheep red blood cells (10$^5$ cells/mouse). On the 4th day after the immunization, sheep red blood cells (10$^8$ cells/mouse) were subcutaneously injected into the footpad of mice for the elicitation to cause a delayed-type hypersensitivity. Test compound was orally administered to the mice once a day from the 0 th day to the 4 th day after the immunization. On the 5th day after the elicitation, the thickness of the mouse footpad was measured to estimate the suppressive effect of the test compound on DTH. The suppressive effect of the test compound was evaluated in terms of the inhibition rate (%) as calculated according to the following equation:

Inhibition rate (%)=100−(T/C×100)

wherein T denotes the thickness of the footpad when the test compound was administered, but C denotes the thickness of the footpad when no test compounnd was administered.

The test results are shown in Table 6 below:

TABLE 6

Effect on delayed-type hypersensitivity in mouse

| Test compound | Dose (mg/mouse) | Period of administration (day) | Inhibition rate (%) |
| --- | --- | --- | --- |
| Delaminomycin A2 sulfuric acid ester (Na salt) | 8.0 | 0–4th | 85.2 |
|  | 2.0 | 0–4th | 56.3 |
|  | 0.5 | 0–4th | −0.7 |
| Delaminomycin B2 sulfuric acid ester (Na salt) | 2.0 | 0–4th | 40.2 |
| Delaminomycin C2 sulfuric acid ester (Na salt) | 2.0 | 0–4th | 35.4 |
| Delaminomycin A2 | 8.0 | 0–4th | 36.1 |
|  | 2.0 | 0–4th | 23.4 |
|  | 0.5 | 0–4th | 7.7 |
| Delaminomycin B2 | 2.0 | 0–4th | 18.4 |
| Delaminomycin C2 | 2.0 | 0–4th | 25.7 |

Sulfuric acid esters of delaminomycin A2, B2 and C2 of the general formula (III) according to the sixth aspect of this invention can similarly be formulated, when they are used as immunosuppressant or as other medicinal agents, and thus the said active compound may be blended with pharmaceutically acceptable, and conventional solid or liquid carrier(s) to prepare a desired pharmaceutical composition.

According to the seventh aspect of this invention, therefore, there is provided a pharmaceutical composition comprising as an active ingredient at least one antibiotic selected from the group consisting of delaminomycin A2 sulfuric acid ester, delaminomycin B2 sulfuric acid ester, delaminomycin C2 sulfuric acid ester and pharmaceutically acceptable salts thereof, and further comprising a pharmaceutically acceptable solid or liquid carrier as mixed with the active ingredient.

The sulfuric acid ester compounds of general formula (III) can also be formulated similarly to the pharmaceutical composition according to the fifth aspect of this invention, and the dosage of the active compounds contained therein may be in the range similar to that given above for the delaminomycin compounds of the general formula (I) or (I') or of the general formula (II).

BRIEF DESCRIPTION OF THE ATTACHED DRAWINGS

Figure 1:
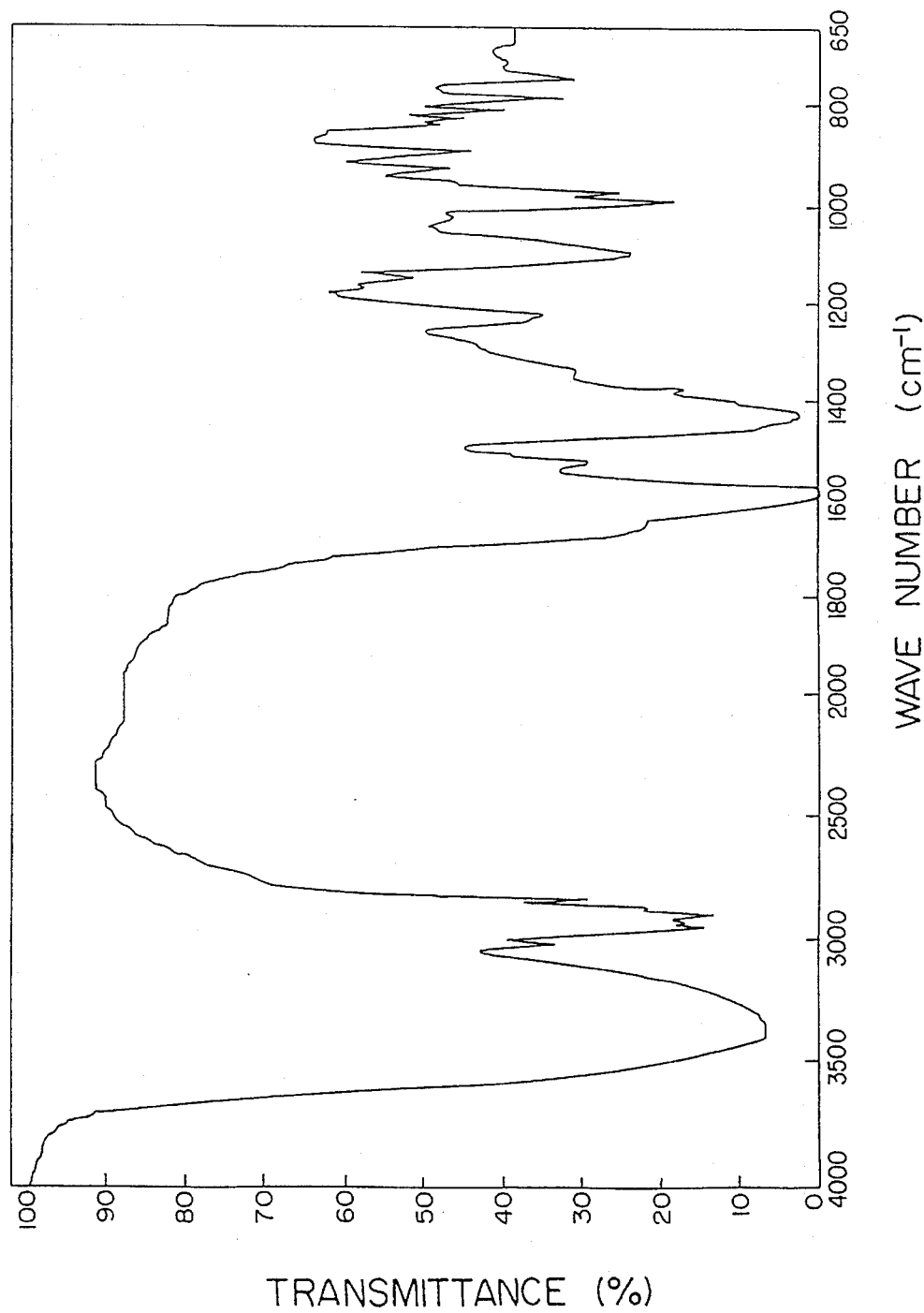
FIG. 1 is an infrared absorption spectrum of delaminomycin A by the KBr disc method.
Figure 2:
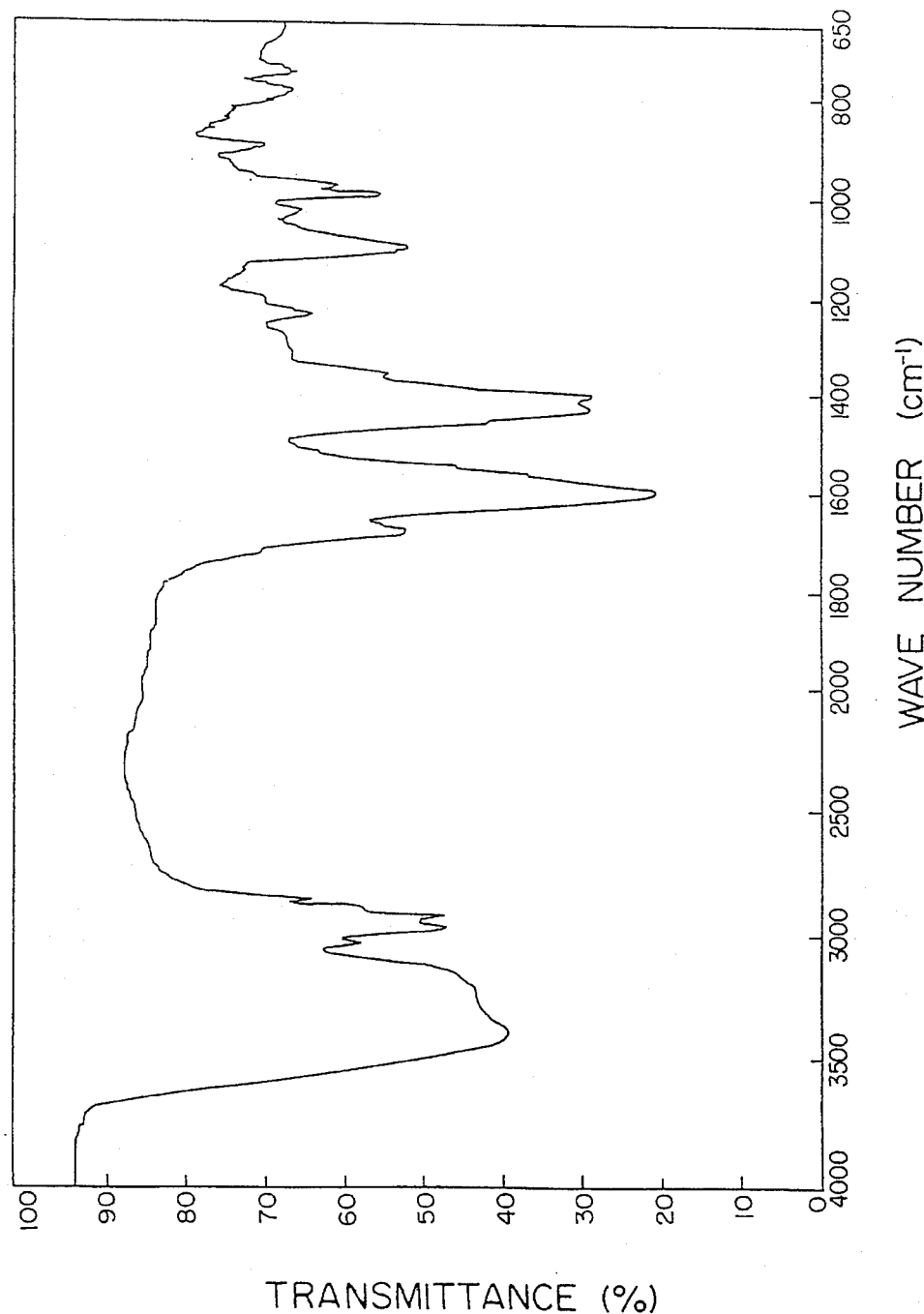
FIG. 2 is an infrared absorption spectrum of delaminomycin B by the KBr disc method.
Figure 3:
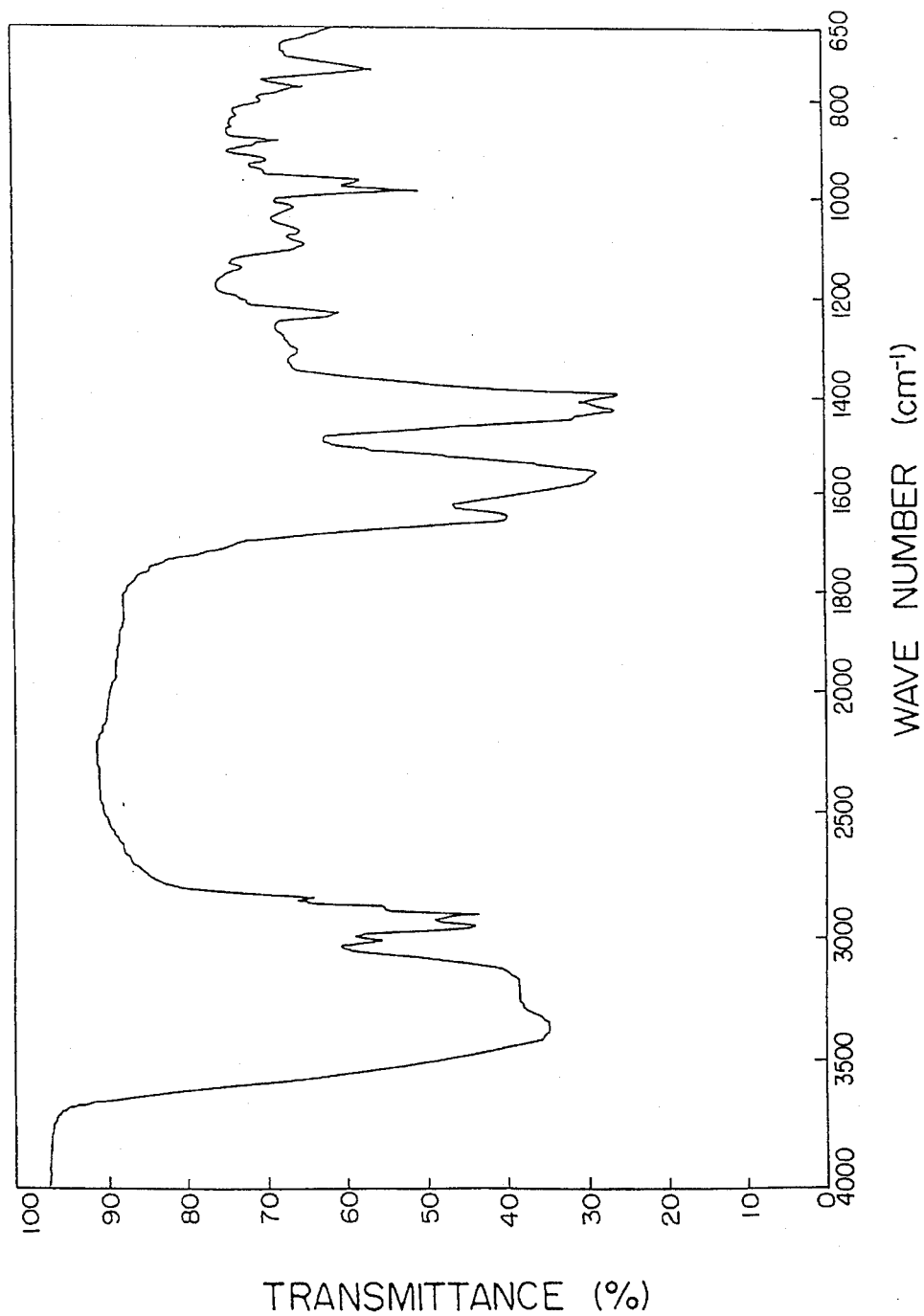
FIG. 3 is an infrared absorption spectrum of delaminomycin C by the KBr disc method.
Figure 4:
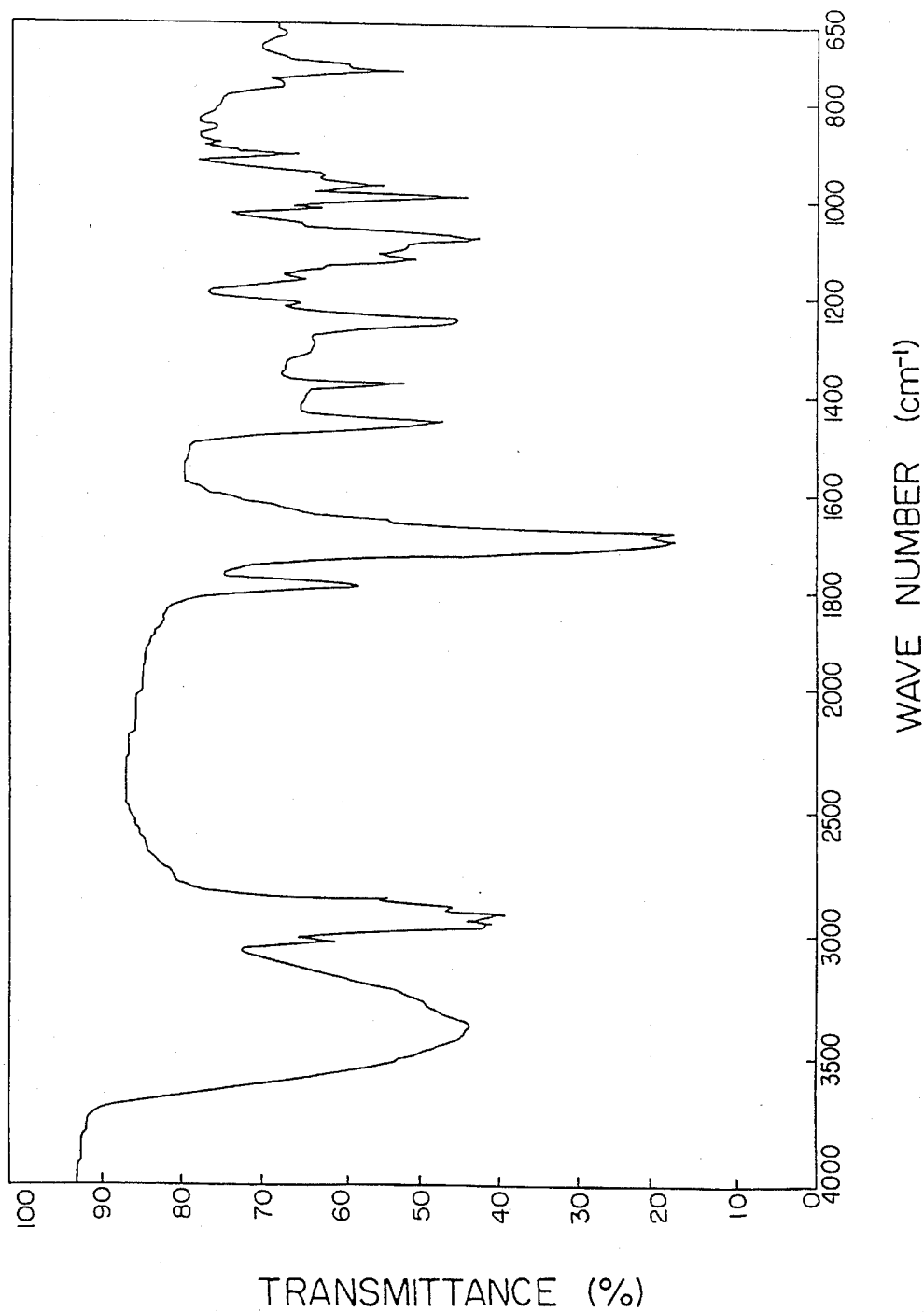
FIG. 4 is an infrared absorption spectrum of delaminomycin A2 by the KBr disc method.
Figure 5:
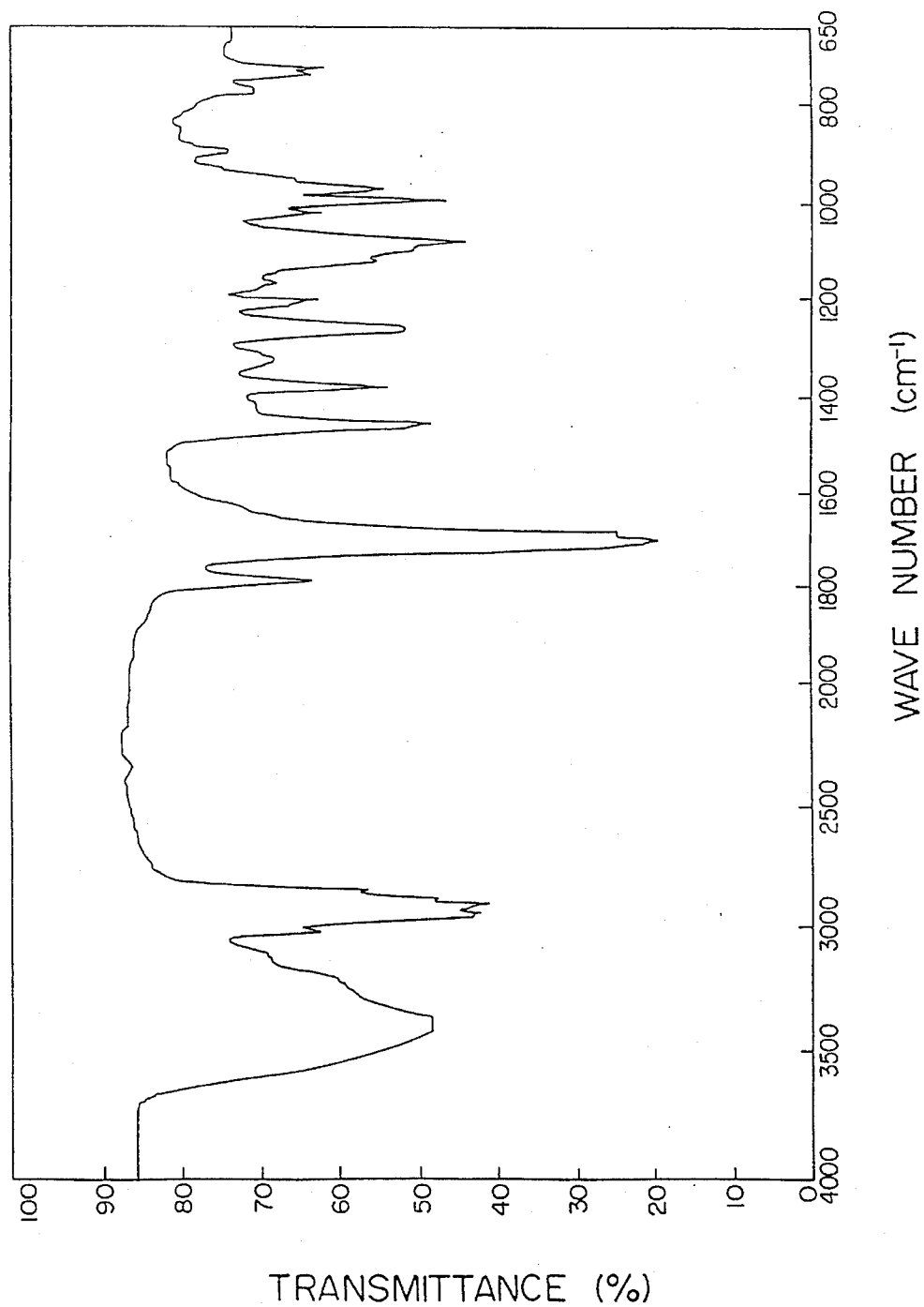
FIG. 5 is an infrared absorption spectrum of delaminomycin B2 by the KBr disc method.
Figure 6:
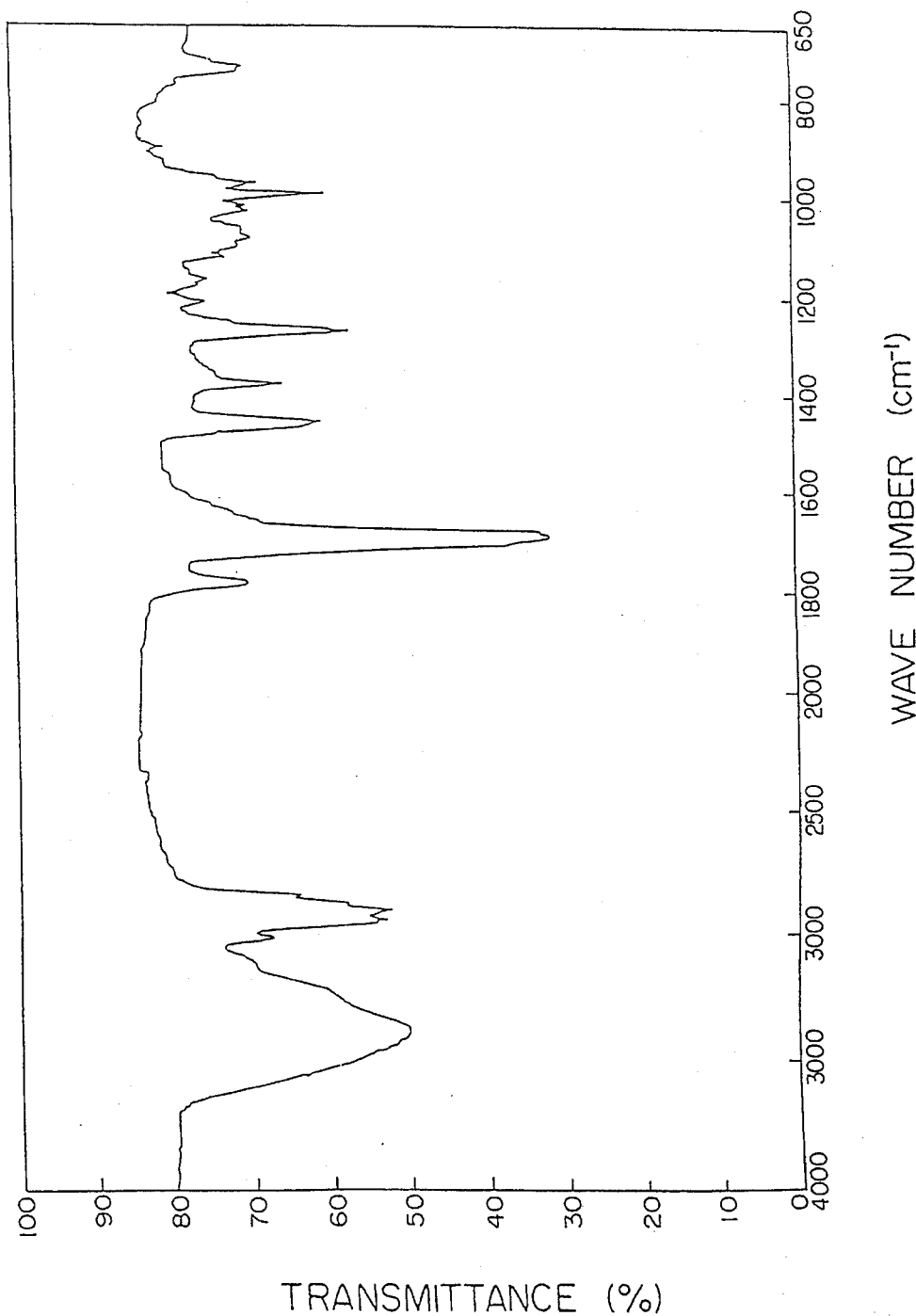
FIG. 6 is an infrared absorption spectrum of delaminomycin C2 by the KBr disc method.
Figure 7:
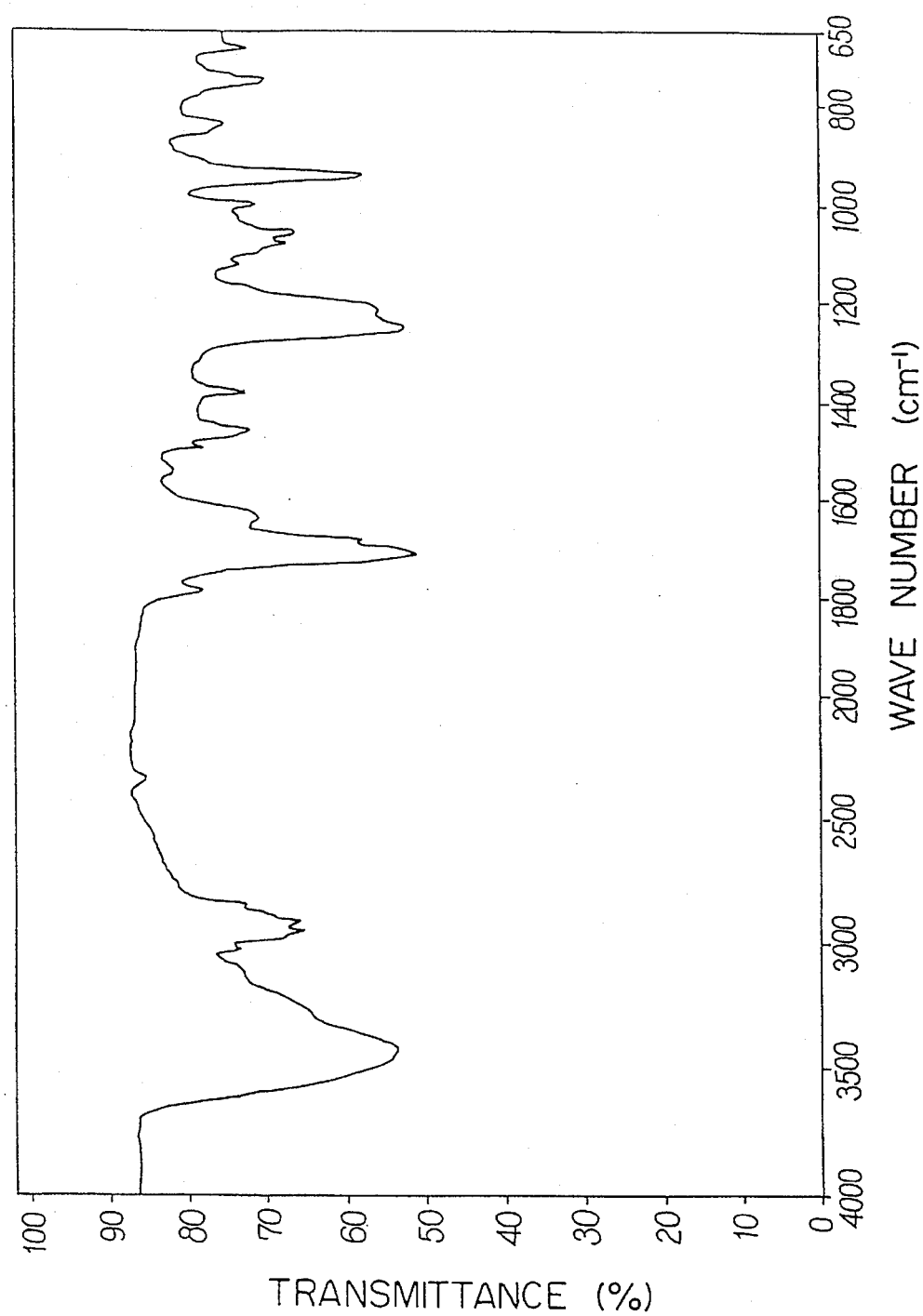
FIG. 7 is an infrared absorption spectrum of sulfuric acid ester of delaminomycin A2 by the KBr disc method.

Now, this invention is further illustrated, but in no way limited, by the following Examples in which "%" is "weight/volume, %".

EXAMPLE 1

This Example illustrates one example of the production of the antibiotics, delaminomycin A, B and C by cultivating the strain MJ202-72F3.

(1) Preparation of Seed culture

The seed medium used herein to prepare the seed culture had the composition as prepared by dissolving the following ingredients in one liter of water without adjustment of pH of the medium.

| | |
| --- | --- |
| Glucose | 1.5% |
| Yeast extract (a product of Daigo Eiyo-sha) | 0.25% |
| Casamino acids (a product of Difco Co.) | 0.25% |
| Calcium carbonate | 0.4% |

Into 500-ml Erlenmeyer flasks were each poured 110 ml portions of the seed medium. After sterilization, the medium in each flask was innoculated with a loopful quantity of a slant culture of *Streptomyces* sp. MJ202-72F3 strain (FERM-P 12674 or FERM BP-4079), and the strain was cultured under rotation on a rotary shaker of 180 rpm at 30° C. for 72 hours to prepare a seed culture.

(2) Cultivation

Medium used herein as the production medium had the composition as prepared by dissolving the undermentioned ingredients in one liter of water without adjustment of pH of the medium. Into 500-ml Erlenmeyer flasks were each poured 110 ml portions of the production medium. After sterilization of the medium, 2.2 ml of the above-mentioned seed culture was added to each flask and cultivated with agitation at 27° C. on a rotary shaker of 180 rpm.

| | |
| --- | --- |
| Glucose | 3.0% |
| Yeast extract (a product of Daigo Eiyo-sha) | 0.5% |
| Casamino acids (a product of Difco Co.) | 0.5% |
| NaNO$_3$ | 0.2% |
| KCl | 0.2% |
| CaCO$_3$ | 0.4% |

(3) Recovery of antibiotics, delaminomycin A, delaminomycin B and/or delaminomycin C After carrying out the cultivation of the strain MJ202-72F3 for 6 days under the conditions of (2) above, about 20 liters of the culture broth were centrifuged (at 3000 rpm, for 15 minutes), and the separated mycelia or cells were treated by extraction with methanol. The methanol was distilled off from the resulting extract, and the remaining aqueous layer was extracted with n-butanol and the n-butanol extract obtained was concentrated to dryness under reduced pressure. About 3 g of the crude material thus obtained from the extract was subjected to centrifugal liquid-liquid partition chromatography (CPC, a product of Sanki Engineering Co.), where the under layer and the upper layer of chloroform-methanol-water (2:2:1) were used as the immobile phase and the mobile phase, respectively, in the ascending mode under the conditions of 20° C., 400 rpm and a flow rate of 1 ml/min. to effect separation and purification of the desired antibiotics. Thus, active fractions which respectively contained delaminomycins A, B and C eluted were obtained, then combined together and concentrated to dryness under reduced pressure.

The roughly purified product (830 mg) so obtained was subjected to gel chromatography using Sephadex LH-20 (a product of Pharmacia Co.), followed by performing the elution with methanol as eluent to collect the fractions containing delaminomycins A, B and C, which were then combined and concentrated to dryness under reduced pressure. The partially purified product containing delaminomycins A, B and C (813 mg) thus obtained was dissolved in methanol, and an aliquot of the resulting methanolic solution was subjected to a high performance liquid chromatography using a column (20 mm ⌀×250 mm) of CAPCELL PAK 5 $C_{18}$ (a product of Shiseido Co.), and the column was then eluted with methanol-25 mM ammonium acetate-acetonitrile (60:10:30) to afford each fraction which contained delaminomycin A, delaminomycin B and delaminomycin C, respectively.

Each of these respective fractions was concentrated to dryness under reduced pressure, and the residue was dissolved in a small amount of methanol and subjected to gel chromatography on Sephadex LH-20 to obtain the respective fractions which contained delaminomycin A, delaminomycin B and delaminomycin C, respectively. By concentrating these respective fractions to dryness under reduced pressure, there were afforded 320 mg of delaminomycin A as a colorless to white solid, 30 mg of delaminomycin B as a colorless to white solid and 13 mg of delaminomycin C as a colorless to white solid.

EXAMPLE 2

This Example illustrates one example of the production of antibiotic, delaminomycin A2 by the ring-closure reaction of delaminomycin A.

Delaminomycin A (220 mg) was dissolved in 3 ml of methanol. After adding thereto 1 ml of 1N hydrochloric acid, the resulting solution was stirred overnight at room temperature. After confirming by TLC that no residual quantity of the starting delaminomycin A was left in the mixture, the reaction solution obtained was concentrated to dryness under reduced pressure. The residue obtained (277 mg) was dissolved in a small quantity of methanol, subjected to high performance liquid chromatography using a silica gel column (20 mm ⌀×250 mm), which was eluted with n-hexane-chloroform-acetonitrile (60:27:13) to obtain a fraction of delaminomycin A2.

This fraction was concentrated to dryness under reduced pressure and the residue was dissolved in a small quantity of methanol, and then the solution was subjected to high performance liquid chromatography using a column (20 mm ⌀×250 mm) of CAPCELL PAK 5 $C_{18}$ (a product of Shiseido Co.), which was eluted with methanol-water (80:20) to obtain a fraction of delaminomycin A2. Concentration of this fraction to dryness under reduced pressure gave a powdery product (64 mg). This powder was again dissolved in a small quantity of methanol and subjected to gel chromatography using Sephadex LH-20, and the resulting fraction containing delaminomycin A2 was concentrated to dryness under reduced pressure to afford 56.5 mg of delaminomycin A2 as a colorless to white solid.

EXAMPLE 3

This Example illustrates one example of the production of antibiotic delaminomycin B2 by the dehydrating ring-closure reaction of delaminomycin B.

About 200 mg of delaminomycin B was dissolved in 3 ml of methanol, to which was then added 1 ml of 1N hydrochloric acid, and the resulting mixture was stirred overnight at room temperature. After confirming by TLC that no residual quantity of the starting delaminomycin B was left in the mixture, the resulting reaction solution was concentrated to dryness under reduced pressure. The residue was dissolved in a small quantity of methanol and subjected to high performance liquid chromatography using a silica gel column (20 mm ⌀×250 mm), which was then eluted with n-hexane-chloroform-acetonitrile (60:27:13) to obtain a fraction of delaminomycin B2. This fraction was subsequently concentrated to dryness under reduced pressure.

The roughly purified product of delaminomycin B2 (65 mg) thus obtained was dissolved in a small quantity of methanol and subjected to high performance liquid chromatography using a column (20 mm ⌀×250 mm) of CAPCELL PAK 5 $C_{18}$ (a product of Shiseido Co.), which was then eluted with methanol-water (80:20) to obtain a fraction of delaminomycin B2. This fraction was concentrated to dryness under reduced pressure, affording 43 mg of a powdery product. This powdery product was dissolved in a small quantity of methanol and subjected to gel chromatography using Sephadex LH-20. The fraction containing delaminomycin B2 separated was concentrated to dryness under a reduced pressure, to yield 34.6 mg of delaminomycin B2 as a colorless to white solid.

EXAMPLE 4

This Example illustrates one example of the preparation of antibiotic, delaminomycin C2 by the dehydrating ring-closure reaction of delaminomycin C.

About 30 mg of delaminomycin C was dissolved in 3 ml of methanol, to which was then added 1 ml of 1N hydrochloric acid, and the mixture was stirred overnight at room temperature. After confirming by TLC that no residual quantity of the starting delaminomycin C was left in the mixture, the resulting reaction solution was subjected to high performance liquid chromatography using a column (20 mm ⌀×250 mm) of CAPCELL PAK 5 $C_{18}$ (a product of Shiseido Co.), which was then eluted with methanol-water (80:20) to methanol by a gradient elution method, to give a fraction of delaminomycin C2.

The fraction thus obtained was concentrated to dryness under reduced pressure to give 11 mg of a powdery product. This powder was dissolved in a small quantity of methanol and subjected to gel chromatography using Sephadex LH-20. The fraction containing delaminomycin C2 thus obtained was concentrated to dryness under reduced pressure, to afford 9.8 mg of delaminomycin C2 as a colorless to white solid.

EXAMPLE 5

To a solution of delaminomycin A2 (350 mg) in chloroform (5 ml) was added a solution of sulfuric acid anhydride-pyridine complex (525 mg) in N,N'-dimethylformamide (3 ml). The resulting mixture was stirred at room temperature for 24 hours to effect the reaction intended. Chloroform was distilled off from the resulting reaction solution, and the concentrated solution was extracted by liquid-liquid partition method using 10% citric acid and ethyl acetate. The ethyl acetate layer containing the desired compound was washed with a saturated aqueous sodium chloride solution and dried over anhydrous sodium sulfate and then concentrated under reduced pressure to give 404 mg (96% yield) of the sulfuric acid ester of delaminomycin A2, which gave a single spot on TLC.

EXAMPLE 6

To a solution of delaminomycin B2 (10 mg) in chloroform (1 ml) was added a solution of sulfuric acid anhydride-pyridine complex (15 mg) in N,N'-dimethylformamide (1 ml). The resulting mixture was stirred at room temperature for 20 hours to effect the reaction intended. Chloroform was distilled off from the resulting reaction solution, and the concentrated solution was extracted by liquid-liquid partition method using 10% citric acid and ethyl acetate. The ethyl acetate layer containing the desired compound was washed with a saturated aqueous sodium chloride solution and dried over anhydrous sodium sulfate and then concentrated under reduced pressure to give 6.6 mg of the sulfuric acid ester of delaminomycin B2, which gave a single spot on TLC.

EXAMPLE 7

To a solution of delaminomycin C2 (12 mg) in chloroform (1 ml) was added a solution of sulfuric acid anhydride-pyridine complex (18 mg) in N,N'-dimethylformamide (1 ml). The resulting mixture was stirred at room temperature for 20 hours to effect the reaction intended. Chloroform was distilled off from the resulting reaction solution and the concentrated solution was extracted by liquid-liquid partition method using 10% citric acid and ethyl acetate. The ethyl acetate layer containing the desired compound was washed with a saturated aqueous sodium chloride solution and dried over anhydrous sodium sulfate and then concentrated under reduced pressure to give 7.9 mg of the sulfuric acid ester of delaminomycin C2, which gave a single spot on TLC.

Industrial Applicability

As has been detailed above, according to this invention, there are obtained the novel antibiotics, delaminomycins A, B, C, A2, B2 and C2, as well as the sulfuric acid esters of delaminomycins A2, B2 and C2, which each have an immunosuppressive activity, an antibacterial activity against gram-positive bacteria and an anticancer activity. These delaminomycins A to C2 and the sulfuric acid esters of delaminomycins A2 to C2 are expected to be useful as an immunosuppressant required for the transplantation of organs or as a therapeutic agent useful for treatments of immuno-defficiency diseases and of local inflammations.

We claim:

1. Antibiotics having an immunosuppressive activity, which are selected from delaminomycin A, delaminomycin B and delaminomycin C represented by the following general formula (I)

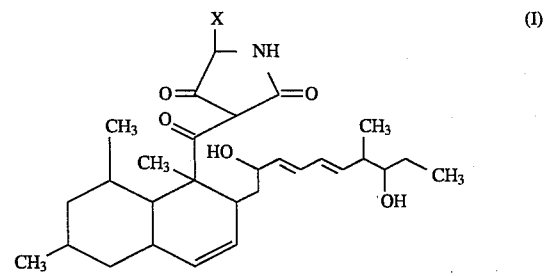

or by the following general formula (I')

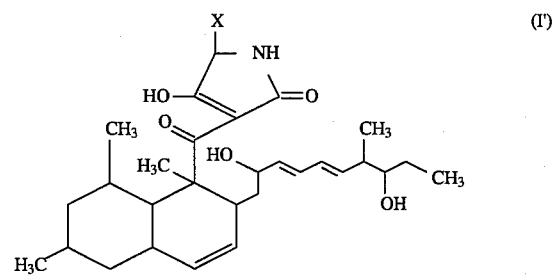

wherein X denotes a hydroxyl group, methoxy group or hydrogen atom, but X is a hydroxyl group for delaminomycin A, a methoxy group for delaminomycin B and a hydrogen atom for delaminomycin C, or salts thereof.

2. Delaminomycin A according to claim 1, which is a compound of the general formula (I) or (I') where X denotes a hydroxyl group.

3. Delaminomycin B according to claim 1, which is a compound of the general formula (I) or (I') where X denotes a methoxy group.

4. Delaminomycin C according to claim 1, which is a compound of the general formula (I) or (I') where X denotes a hydrogen atom.

5. A pharmaceutical composition comprising as an active ingredient at least one antibiotic selected from the group consisting of delaminomycin A, delaminomycin B, and delaminomycin C, or a pharmaceutically acceptable salt of said antibiotic, and further comprising a pharmaceutically acceptable solid or liquid carrier as mixed with the active ingredient.

* * * * *